(12) United States Patent
Lapota et al.

(10) Patent No.: US 9,772,288 B1
(45) Date of Patent: Sep. 26, 2017

(54) AUTONOMOUS BIOBUOY SYSTEMS AND METHODS

(71) Applicant: SPAWAR Systems Center Pacific, San Diego, CA (US)

(72) Inventors: David Lapota; Gregory W. Anderson, San Diego, CA (US)

(73) Assignee: The United States of America as represented by Secretary of the Navy, Washington, DC (US)

( * ) Notice: Subject to any disclaimer, the term of this patent is extended or adjusted under 35 U.S.C. 154(b) by 0 days.

(21) Appl. No.: 15/386,117

(22) Filed: Dec. 21, 2016

(51) Int. Cl.
  *G01N 21/64* (2006.01)
(52) U.S. Cl.
  CPC ....... *G01N 21/6486* (2013.01); *G01N 21/645* (2013.01); *G01N 2021/6482* (2013.01); *G01N 2201/0221* (2013.01); *G01N 2201/069* (2013.01)
(58) Field of Classification Search
  CPC ............. G01N 21/6486; G01N 21/645; G01N 2021/6482; G01N 2201/0221; G01N 2201/069
  See application file for complete search history.

(56) References Cited

U.S. PATENT DOCUMENTS

| | | | | |
|---|---|---|---|---|
| 4,293,225 | A | * | 10/1981 | Wheaton .............. G01N 21/645 250/461.1 |
| 4,350,890 | A | * | 9/1982 | Geelhood ................. G01J 1/04 250/361 C |
| 4,394,573 | A | * | 7/1983 | Correa ................... G01N 21/53 250/253 |
| 6,166,496 | A | | 12/2000 | Lys et al. |
| 6,211,626 | B1 | | 4/2001 | Lys et al. |
| 6,285,807 | B1 | | 9/2001 | Walt et al. |
| 6,292,901 | B1 | | 9/2001 | Lys et al. |
| 6,340,868 | B1 | | 1/2002 | Lys et al. |
| 6,459,919 | B1 | | 10/2002 | Lys et al. |
| 6,520,105 | B2 | | 2/2003 | Koda et al. |
| 6,528,954 | B1 | | 3/2003 | Lys et al. |
| 6,577,080 | B2 | | 6/2003 | Lys et al. |
| 6,720,745 | B2 | | 4/2004 | Lys et al. |
| 7,038,398 | B1 | | 5/2006 | Lys et al. |
| 7,132,804 | B2 | | 11/2006 | Lys et al. |
| 7,180,252 | B2 | | 2/2007 | Lys et al. |
| 7,221,104 | B2 | | 5/2007 | Lys et al. |
| 7,308,296 | B2 | | 12/2007 | Lys et al. |
| 7,352,339 | B2 | | 4/2008 | Morgan et al. |
| 7,453,217 | B2 | | 11/2008 | Lys et al. |
| 7,525,254 | B2 | | 4/2009 | Lys et al. |

(Continued)

*Primary Examiner* — Christine Sung
(74) *Attorney, Agent, or Firm* — SPAWAR Systems Center Pacific; Kyle Eppele

(57) ABSTRACT

An autonomous biobuoy system and methods for detecting characteristics of a marine environment, the system involving: a light source comprising a blue light emitting diode; a detector assembly for detecting the at least one characteristic of the marine environment, the detector assembly having a single photodiode configured to detect stimulated bioluminescence and transmissivity in response to the light source, the detector assembly configured to generate at least one detector assembly output signal responsive to at least one detected characteristic; and a transmitter coupled with the detector assembly for transmitting the at least one detector assembly output signal.

20 Claims, 16 Drawing Sheets

(56) References Cited

U.S. PATENT DOCUMENTS

| | | |
|---|---|---|
| 7,559,236 B1 | 7/2009 | Lapota et al. |
| 7,598,686 B2 | 10/2009 | Lys et al. |
| 7,690,247 B1 * | 4/2010 | Lapota .................. G01C 13/00 |
| | | 73/170.29 |
| 7,953,326 B2 | 5/2011 | Farr et al. |
| 8,154,414 B2 | 4/2012 | Levinson |
| 8,188,878 B2 | 5/2012 | Pederson et al. |
| 8,654,319 B2 | 2/2014 | Rao et al. |
| 8,902,076 B2 | 12/2014 | Pederson et al. |
| 9,203,524 B2 | 12/2015 | Simpson et al. |
| 9,294,201 B2 | 3/2016 | Farr et al. |
| 2001/0028227 A1 | 10/2001 | Lys et al. |
| 2001/0039910 A1 | 11/2001 | Koda et al. |
| 2002/0047646 A1 | 4/2002 | Lys et al. |
| 2002/0113555 A1 | 8/2002 | Lys et al. |
| 2003/0011538 A1 | 1/2003 | Lys et al. |
| 2003/0076281 A1 | 4/2003 | Morgan et al. |
| 2003/0100837 A1 | 5/2003 | Lys et al. |
| 2004/0155609 A1 | 8/2004 | Lys et al. |
| 2004/0257007 A1 | 12/2004 | Lys et al. |
| 2005/0063194 A1 | 3/2005 | Lys et al. |
| 2005/0151489 A1 | 7/2005 | Lys et al. |
| 2006/0250276 A1 | 11/2006 | Levinson |
| 2007/0183782 A1 * | 8/2007 | Farr ....................... H04B 13/02 |
| | | 398/104 |
| 2007/0188427 A1 | 8/2007 | Lys et al. |
| 2008/0085504 A1 * | 4/2008 | Bjorndal ............ G01N 33/1866 |
| | | 435/4 |
| 2008/0183081 A1 | 7/2008 | Lys et al. |
| 2008/0310850 A1 | 12/2008 | Pederson et al. |
| 2009/0105537 A1 | 4/2009 | Gat et al. |
| 2011/0060551 A1 | 3/2011 | Elhajj |
| 2011/0229141 A1 | 9/2011 | Chave et al. |
| 2011/0273705 A1 | 11/2011 | Rao et al. |
| 2012/0230696 A1 | 9/2012 | Pederson et al. |
| 2013/0327961 A1 * | 12/2013 | Tedetti ................. G01N 21/645 |
| | | 250/461.1 |
| 2014/0203184 A1 | 7/2014 | Purdy et al. |
| 2014/0248058 A1 | 9/2014 | Simpson et al. |
| 2015/0078123 A1 | 3/2015 | Batcheller et al. |
| 2015/0086213 A1 | 3/2015 | Pederson et al. |
| 2015/0372769 A1 | 12/2015 | Farr et al. |
| 2016/0170060 A1 * | 6/2016 | Hopewell ................ G01V 1/38 |
| | | 367/15 |

* cited by examiner

AUTONOMOUS BIOBUOY SYSTEMS AND METHODS

FEDERALLY-SPONSORED RESEARCH AND DEVELOPMENT

The United States Government has ownership rights in the subject matter of the present disclosure. Licensing inquiries may be directed to Office of Research and Technical Applications, Space and Naval Warfare Systems Center, Pacific, Code 72120, San Diego, Calif., 92152; telephone (619) 553-5118; email: ssc_pac_t2@navy.mil. Reference Navy Case No. 102,529.

BACKGROUND OF THE INVENTION

Technical Field

The present disclosure technically relates to buoys. Particularly, the present disclosure technically relates to buoy systems and methods. More particularly, the present disclosure technically relates to buoy systems and methods for performing measurements.

Description of Related Art

In the related art, bioluminescence involves light being generated by a chemical reaction within an organism, such as a marine organism, wherein chemical energy is converted into light energy. The chemical that produces the light is luciferin, which the organism acquires by diet or by internal synthesis. A chemical known as luciferase catalyzes the oxidation of luciferin to produce the light. Examples of marine organisms that evince bioluminescence include dinoflagellates and zooplankton. Dinoflagellate "blooms," i.e., population congregations having a high density such that the congregations discolor a marine environment, e.g., a red bloom or a brown bloom forming a "red tide," have been observed to degrade fluid quality and produce toxins harmful to other marine organisms. Such toxins can even affect humans, such as by paralytic shellfish poisoning. Bioluminescence diminishes in the presence of toxic chemicals. However, a related art challenge includes further effectively sensing bioluminescence to detect toxins in marine environments or any body of water, such as oceans, seas, lakes, ponds, sloughs, rivers, canals, streams, creeks, dams, and the like.

Additionally, studying bioluminescence over an extended period of time to determine the manner in which the populations of bioluminescent organisms vary over time has been performed in the related art. Determining the manner in which populations of bioluminescent organisms vary with respect to changes in fluid temperature and fluid clarity has also been performed. While some related art oceanographic studies have focused on the distribution of bioluminescence in the marine environment, a further understanding of the seasonal characteristics thereof remains. Related art studies have been limited in duration, e.g., usually less than one or two years with long intervals between sets of measurements, as well as in developing any useful methods for actually quantifying bioluminescence. Another challenge in the related art is further improving the quantification of marine bioluminescence over time and with respect to fluid temperature and clarity.

Further, some related art techniques involve tethering a device to a vehicle for gathering data and powering the device by way of power onboard the vehicle. Further, some related art biobuoys involve the use of a photomultiplier. Another challenge in the related art is reducing the size of a device and reducing the number of persons to manually assist in the deployment thereof. The related art has also experienced challenges, such as further effectively sensing bioluminescence to detect toxins in marine environments or any body of water, such as oceans, seas, lakes, ponds, sloughs, rivers, canals, streams, creeks, dams, and the like, as well as an absence of a suitable device for autonomously conducting extended duration marine studies of bioluminescence.

Therefore, a need exists to develop systems and methods that improve effectively sensing bioluminescence to detect toxins in marine environments or any body of fluid and that autonomously conduct extended duration marine studies of bioluminescence.

SUMMARY OF THE INVENTION

To address at least the needs and challenges in the related art, the autonomous biobuoy systems and methods of the present disclosure are configured to effectively sense bioluminescence and transmissivity for detecting toxins in marine environments.

In accordance with an embodiment of the present disclosure, an autonomous biobuoy system for detecting characteristics of a marine environment, the system comprising: a light source comprising a blue light emitting diode; a detector assembly for detecting the at least one characteristic of the marine environment, the detector assembly comprising a single photodiode configured to detect stimulated bioluminescence and transmissivity in response to the light source, the detector assembly configured to generate at least one detector assembly output signal responsive to at least one detected characteristic; and a transmitter coupled with the detector assembly for transmitting the at least one detector assembly output signal.

BRIEF DESCRIPTION OF THE DRAWING

The above, and other, aspects, features, and uses of several embodiments of the present disclosure are further understood from the following Detailed Description of the Invention as presented in conjunction with the following several figures of the Drawing.

Figure 1:
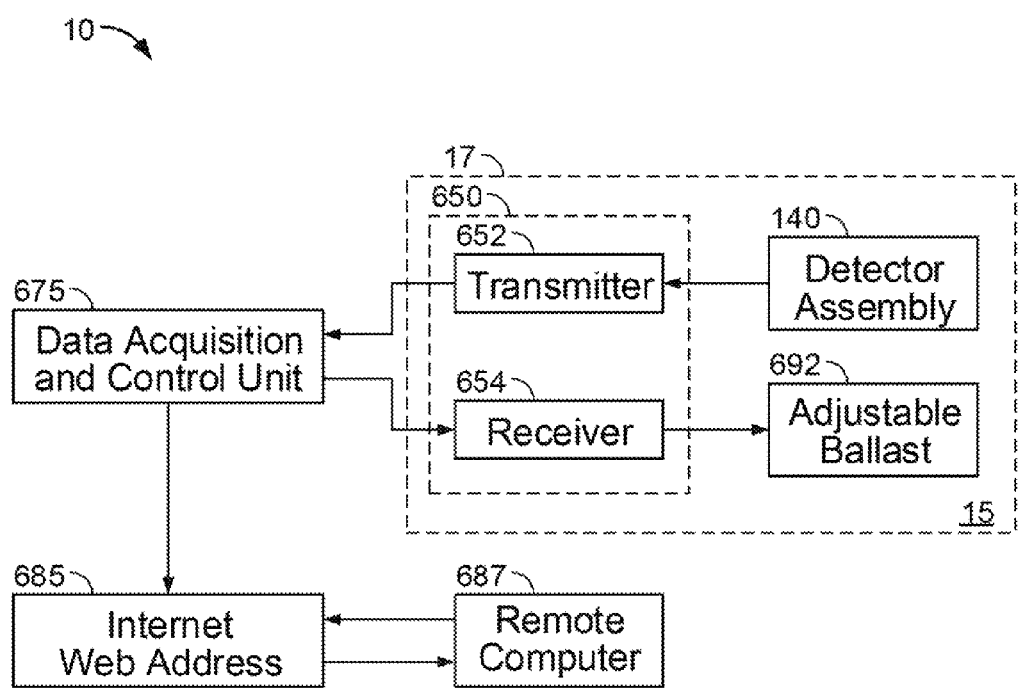
FIG. 1 is a schematic diagram illustrating an autonomous biobuoy system, as known in the prior art and capable of implementing an embodiment of the present disclosure.

Corresponding reference numerals or characters indicate corresponding components throughout the several figures of the Drawings. Elements in the several figures are illustrated for simplicity and clarity and have not necessarily been drawn to scale. For example, the dimensions of some of the elements in the figures may be emphasized relative to other elements for facilitating understanding of the various presently disclosed embodiments. Also, common, but well-understood, elements that are useful or necessary in a commercially feasible embodiment are often not depicted in order to facilitate a less obstructed view of these various embodiments of the present disclosure.

DETAILED DESCRIPTION OF THE INVENTION

Features of the systems and methods of the present disclosure include, but are not limited to, using systems and methods configured to detect bioluminescence for assessing the environmental characteristics of a marine environment, such as for health reasons, testing the marine environment for the presence of toxins, e.g., in bodies of fluid, such as lakes, streams, rivers, and oceans, and the like.

Referring to FIGS. 1, 2, 3, 4, and 5, together, these diagrams generally illustrate an autonomous biobuoy system 10 for detecting at least one characteristic of a marine environment 15, such as a marine biosphere, as known in the prior art and capable of implementing an embodiment of the present disclosure. Still referring to FIGS. 1, 2, 3, 4, and 5 together, the marine environment 15 has a surface 17 and may have a corrosive content, such as salt, e.g., NaCl. In general, the autonomous biobuoy system 10 comprises at least one corrosion-resistant material, such as aluminum, bronze, brass, stainless steel, titanium, a suitable ceramic, a suitable polymer, such as a plastic, a composite material, and the like, for reducing corrosive attack by the marine environment 15. The biobuoy system 10 is configured to detect at least one characteristic and comprises at least one of bioluminescence in the marine environment 15, temperature of marine environment 15, opaqueness of marine environment 15, transmissivity of the marine environment 15, and a presence of a contaminant, such as petroleum, oil, or lubricant on the surface 17. However, understood is that other characteristics may be detected as well, and such detection is encompassed by the present disclosure. For example, the biobuoy system 10 is further configurable, by way of at least one selectable detector, to detect at least one of pressure, salinity, and/or other characteristic of interest.

Referring to FIGS. 1, 2, 3, and 4, together, the biobuoy system 10 comprises a housing 20 that includes a tubular member 30. The tubular member 30 has a first end 40 and a second end 50. Also, the tubular member 30 defines an interior 60, a wall 61, an interior surface 62 of the wall 61, and an exterior surface 63 of the wall 61. A partition plate 64, integrally coupled with the interior surface 62 and extending therearound, is disposed in the interior 60. The partition plate 64 divides the interior 60 into a first compartment 65a and a second compartment 65b. The compartment 65a is fluid-tight. An intake port 68 is formed through the tubular member 30, the intermediate partition plate 64 and the second end 50. The tubular member 30 may take any shape in a transverse cross-section, such as a circular shape, a square shape, a triangular shape, and any other suitable shape.

Still referring to FIGS. 1, 2, 3, and 4, together, an outlet port 69 is formed through the tubular member 30, the intermediate intake port 68, and the second end 50. A generally disk-shaped hollow cap 70, defining a chamber 80 therein, is mounted, such as by welding, on the first end 40 of the tubular member 30. The cap 70 serves as a flotation device for maintaining buoyancy of the housing 20 in relation to the marine environment 15. In this regard, the cap 70 comprises a suitable material having a specific gravity in a range of less than approximately 1000 kilograms/cubic meter, such as at least one of solid cork having a specific gravity in a range of approximately 200 kg/m$^3$, wood having a specific gravity in a range of approximately 673 kg/m$^3$, and any other suitable materials having a specific gravity of in a range of less than approximately 1000 kg/m$^3$ for facilitating floatation of the biobuoy system 10 in relation to a fluid, such as marine fluid.

Still referring to FIGS. 1, 2, 3, and 4, together, a plurality of spaced-apart openings 90 is formed through the cap 70 and extending around the perimeter of the cap 70. In addition, the cap 70 defines a platform 95 thereon and an optical window 97 therein. Although it is contemplated that the biobuoy system 10 is deployable in an ocean, appreciated is that the biobuoy system 10 is deployable in relation to lakes, bays, rivers, and the like for detecting bioluminescent organisms therein as well as other characteristics of interest, e.g., temperature of marine environment 15, opaqueness of marine environment 15, transmissivity of the marine environment 15, and a presence of a contaminant, such as petroleum, oil, and lubricant, on the surface 17.

Referring to FIGS. 2, 3, 4 and 5, together, the biobuoy system 10 comprises a weighted ballast member 100 which is coupled with the second end 50 of the tubular member 30 for stabilizing the housing 20 in the marine environment 15, such as a body of fluid having wave action tending to rock the biobuoy system 10. The ballast member 100 is "weighted" in that the ballast member 100 has a specific gravity in a range greater than that of the marine environment 15 and is sized such that the tubular member 30 is stabilized, thereby preventing sinking of the system 10 in the marine environment 15. With regard to enhancing stabilization of the system 10, the ballast member 100 lowers the center of gravity (CG) of the housing 20 to improve the stabilization of housing 20, particularly during a pronounced wave action.

Still referring to FIGS. 2, 3, 4, and 5 together, improving stabilization facilitates obtaining more reliable or repeatable test results, e.g., by preventing adverse effects of the pronounced wave action. The biobuoy system 10 is deployable in relation to the marine environment 15 by any suitable technique, such jettisoning from a helicopter 110, an airplane 120, a boat 130, an unmanned vehicle (not shown), an unmanned aircraft, (not shown) and an unmanned seacraft (not shown). Alternatively, the biobuoy system 10 is deployable by lowering the system 10 in relation to the marine environment 15 from a helicopter 110, an airplane 120, a boat 130, an unmanned vehicle (not shown), an unmanned aircraft, (not shown) and an unmanned seacraft (not shown) by using a winch mechanism (not shown).

Still referring to FIGS. 2, 3, 4 and 5, together, the systems and methods of the present disclosure involve detection of bioluminescence. For example, bioluminescence diminishes in the presence of toxic chemicals; therefore, the systems and methods of the present disclosure involve using the phenomenon of bioluminescence for indicating fluid quality. Further, the systems and methods of the present disclosure involve conducting basic research of bioluminescence. For example, the systems and methods of the present disclosure are configured to study changes in bioluminescence over time and to study bioluminescence as a function of temperature, marine opaqueness, and salinity. Hence, the systems and methods of the present disclosure are configured to detect bioluminescence for enhancing environmental fluid quality monitoring and for the purpose of marine research.

Still referring to FIGS. 2, 3, 4 and 5, together, the biobuoy system 10 comprises a detector assembly 140 disposed in the interior 60 of the tubular member 30 for performing measurements of bioluminescence and other characteristics in the marine environment 15. The detector assembly 140 comprises a light-sensitive bioluminescence detector assembly 150. The light-sensitive bioluminescence detector assembly 150 is disposed in the tubular member 30 between the intake port 68 and the outlet port 69 for detecting bioluminescence. The light sensitive detector assembly 150 comprises a test chamber 160 defining a light-tight or darkened cavity 165 therein for receipt of fluid in which bioluminescent marine organisms (not shown) may be suspended. By example only, the cavity 165 has a volume of approximately 25 ml. An inlet opening (not shown) and an outlet opening (not shown) are in communication with cavity 165 for allowing ingress and egress of fluid, such as marine fluid.

Still referring to FIGS. 2, 3, 4 and 5, together, the biobuoy system 10 comprises a pump assembly 170 coupled with the outlet opening of the cavity 165 for suctioning the fluid, such as marine fluid, therethrough. The pump assembly 170 comprises an electric pump 180 having a suction end 185 coupled with the outlet opening of cavity 165. The pump 180 is in fluid communication with the fluid in the cavity 165 for suctioning the fluid therethrough. The pump 180 also has a discharge end 187. A mesh filter 188 is disposed at the inlet opening of cavity 165 for filtering debris from the fluid entering the cavity 165, thereby enhancing accuracy, reliability, and validity of test results. A light-sensitive detector, such as a photodetector 190, is coupled with the filter 188, e.g., at the top of the filter 188, and is in communication with the cavity 165 for sensing light emitted by bioluminescent marine organisms therein. The photodetector 180 comprises a photodetector tube having a diameter of approximately 1-inch, such as a photodetector tube manufactured by Hamamatsu Photonics, K.K., Hamamatsu City, Japan, by example only.

Still referring to FIGS. 2, 3, 4 and 5, together, the pump 180 is configured to suction a liquid, such as marine fluid, containing any bioluminescent organisms, through the intake port 68 along a first flow path 195. The liquid then flows through the filter 188 and into the cavity 165 for detection of bioluminescence that may be emitted therein. By example only, the pump 180 suctions fluid through the cavity 165 at a constant rate, such as a constant flow rate of approximately 0.25 L/s, whereby test results do not vary as a function of varying flow rate. A constant flow rate allows for easier data analysis. As the liquid enters the cavity 165, any living and healthy bioluminescent organisms therein emit light detectable by the photodetector 190.

Still referring to FIGS. 2, 3, 4 and 5, together, bioluminescence of the marine organisms present in the cavity 165 is caused either by the organisms impacting the mesh filter 188 or by a turbulent motion of the liquid passing through the cavity 165. Turbulence associated with fluid mixing in the cavity 165 also stimulates bioluminescent organisms, such as plankton and single-cell dinoflagellates, to emit light within the darkened cavity 165. Also, as fluid is suctioned through the cavity 165, small bioluminescent organisms, such as zooplankton, are sampled and contribute to an overall bioluminescent signal. In response to any bioluminescence, the photodetector 190 generates an output signal that is transmitted to an electronics unit 200, such as by way of an electrical conduit (not shown). The electronics unit 200 is disposed on the platform 95 defined by the cap 70, by example only.

Still referring to FIGS. 2, 3, 4 and 5, together, the biobuoy system 10 is configured to detect fluid clarity, opaqueness, transmissivity, as well as bioluminescence, whereby at least one region of plankton concentration in the marine environment 15 is indicated. The biobuoy system 10 is further configured to detect a decrease in fluid clarity, opaqueness, transmissivity, as well as bioluminescence, whereby at least one region of increased plankton concentration in the marine environment 15 is indicated, e.g., indicating a "red tide" condition, wherein fluid quality is decreased. Identifying the at least one region of increased plankton concentration facilitates performance of environmental research projects, such as by facilitating investigation of variation in plankton populations and their environmental impact over time.

Still referring to FIGS. 2, 3, 4 and 5 together, the biobuoy system 10 comprises a transmissometer assembly 210 that is coupled with the exterior wall 64 of tubular member 30, such as by a plurality of bands 194, for detecting fluid clarity, opaqueness, transmissivity. The transmissometer assembly 210 is in fluid communication with the marine environment 15 via the port 68. The transmissometer assembly 210 comprises a generally elongated body 220 having a first leg portion 225 and a second leg portion 227 outwardly projecting therefrom. A light source L (FIG. 15), such as a light-emitting diode (LED) 230, e.g., a blue light emitting diode which emits a monochromatic light signal of wave length between 420 nm to 480 nm, is coupled with the second leg portion 227 and is in optical communication with the fluid that is exteriorly disposed in relation to the tubular member 30. The LED 230 is coupled with the electronics unit 200, such as by way of an electrical conduit (not shown) for transmitting electrical power thereto. A first window 240 is configured to cover and seal the LED 230, thereby protecting the LED 230 from corrosive attack, e.g., from fluid and corrosive debris present in the marine environment 15. By example only, the LED 230 emits a monochromatic red light signal having a wavelength with a range of approximately 620 nm to approximately 690 nm. In one embodiment, the wavelength is a range of approximately 680 nm. The LED 230 comprises a suitable LED suitable, such as an LED from Wet Labs, Inc., Philomath, Oreg., U.S.A.

Still referring to FIGS. 2, 3, 4 and 5, together, the transmissometer assembly 210 further comprises a transmissometer light detector 250 that is aligned with the LED 230 and that is in optical communication therewith. A second window 255 covers and seals the light detector 250, thereby protecting the light detector 250 from corrosive attack, e.g., from fluid and corrosive debris present in marine environment 15. The amount of light emitted by the LED 230 that is detected by light detector 250 is attenuated by the amount of clarity or opaqueness therebetween, whereby detected light is obtained. Thus, the detected light indicates fluid clarity or opaqueness of marine environment 15. Light emitted by the LED 230 follows a light path 257 to reach the light detector 250. The light detector 250 generates a light detector output signal which is conducted by an electrical conduit (not shown) to the electronics unit 200. Moreover, the body 220 defines a hollow portion 260 therein that is in fluid communication with the outlet end 187 of the pump 180. The hollow portion 260 is in fluid communication with the outlet end 187 of the pump 180 by way of the tube 265.

Still referring to FIGS. 2, 3, 4 and 5, together, a first channel 280, angled to align with the first window 240, is formed in the body 220 and is in communication with the hollow portion 260. Also, a second channel 270, angled to align with the second window 255, is formed in the body 220 and is in communication with the hollow portion 260. As the pump 180 suctions fluid through the cavity 165 and into the hollow portion 260, the fluid flows through the first channel 280 and the second channel 270 to respectively impinge the first window 240 and the second window 255. As fluid flows through the first channel 280 and the second channel 270, the fluid simultaneously flows from the suction end 185 of the pump 180 and exits the outlet port 69.

Still referring to FIGS. 2, 3, 4 and 5, together, as the fluid respectively impinges the first window 240 and the second window 255, the fluid washes corrosive particles and corrosive debris from the windows 240 and 255. Thus, the channels 270 and 280, in combination with the pump 180, function to automatically wash windows 240 and 255, thereby preventing the blockage of the transmission of light from the LED 230 or the receipt of light by the light detector 250. In the system 10, optimizing the transmission of a light signal emitted by the LED 230 and the receipt of a light signal received by the light detector 250 provides an accurate measurement in relation to the clarity of fluid residing therebetween for at least the reason that a presence of corrosive particles and corrosive debris on either the first window 240 or the second window 255 would otherwise interfere with such measurement.

Still referring to FIGS. 2, 3, 4 and 5, together, the biobuoy system 10 comprises a temperature thermistor 290 disposed in the second compartment 65b of the tubular member 30, and in fluid communication with the marine environment 15 via the intake port 68, and the temperature comprises a thermistor 290 for measuring temperature in the marine environment 15 by measuring the fluid temperature within the second compartment 65b. Also, the biobuoy system 10 comprises a conductivity detector 300, e.g., a salinity detector, disposed in the second compartment 65b and which is in fluid communication with the marine environment 15 via the intake port 68, for measuring electrical conductivity, e.g., salinity, of the marine environment 15 by measuring electrical conductivity of the fluid within the second compartment 65b.

Still referring to FIGS. 2, 3, 4 and 5 together, the biobuoy system 10 comprises a depth detector 310, disposed in the second compartment 65b, and which is in fluid communication with the marine environment 15 via the intake port 68, for measuring depth of the housing 20 in the marine environment 15 by measuring fluid pressure or hydraulic head in the second compartment 65b. In this manner, the light-sensitive detector assembly 150, the thermistor 290, the conductivity detector 300, and the depth detector 310, together, detect a plurality of characteristics related to the marine environment 15 by taking measurements in the marine environment 15. Each of the light-sensitive detector assembly 150, the thermistor 290, the conductivity detector 300, and the depth detector 310, is coupled with the electronics unit 200, by way of respective conduits of a plurality of electrical conduits (not shown). Such data signals, received by electronics unit 200, are transformed by the electronics unit 200 into data signals appropriate for radio frequency transmission.

Still referring to FIGS. 2, 3, 4 and 5, together, as the pump 180 operates, fluid is suctioned through the intake port 68 and along the flow path 195. The fluid then flows through the mesh filter 188, thereby blocking debris, but not blocking the bioluminescent organisms, from entering the cavity 165. As the fluid flows from the cavity 165 and through the pump 180, a first portion of the fluid enters the hollow portion 260 of the body 220 and a second portion exits the outlet port 69. As the fluid enters the hollow portion 260, the fluid flows through the first channel 270 and the second channel 280. Fluid flowing through the first channel 270 and the second channel 280 impinges the first window 240 and the second window 255 for washing the windows 240 and 255, whereby the windows 240 and 255 remain debris-free.

Still referring to FIGS. 2, 3, 4 and 5, together, as fluid washes the windows 240 and 255, the fluid flows toward the outlet port 69 and then exits there through generally along the second flow path 315. Also, as the housing 20 is deployed in the marine environment 15, the second compartment 65b fills with fluid that enters through the intake port 68. In this manner, the cavity 165, the pump 180, the LED 230, the light-sensitive light detector 250, the thermistor 270, the conductivity detector 300, and the depth detector 310, together, are immersed in fluid from the marine environment 15 by way of fluid entering the intake port 68. These components are immersed in fluid in order to obtain accurate measurements of characteristics in the marine environment 15.

Figure 2:
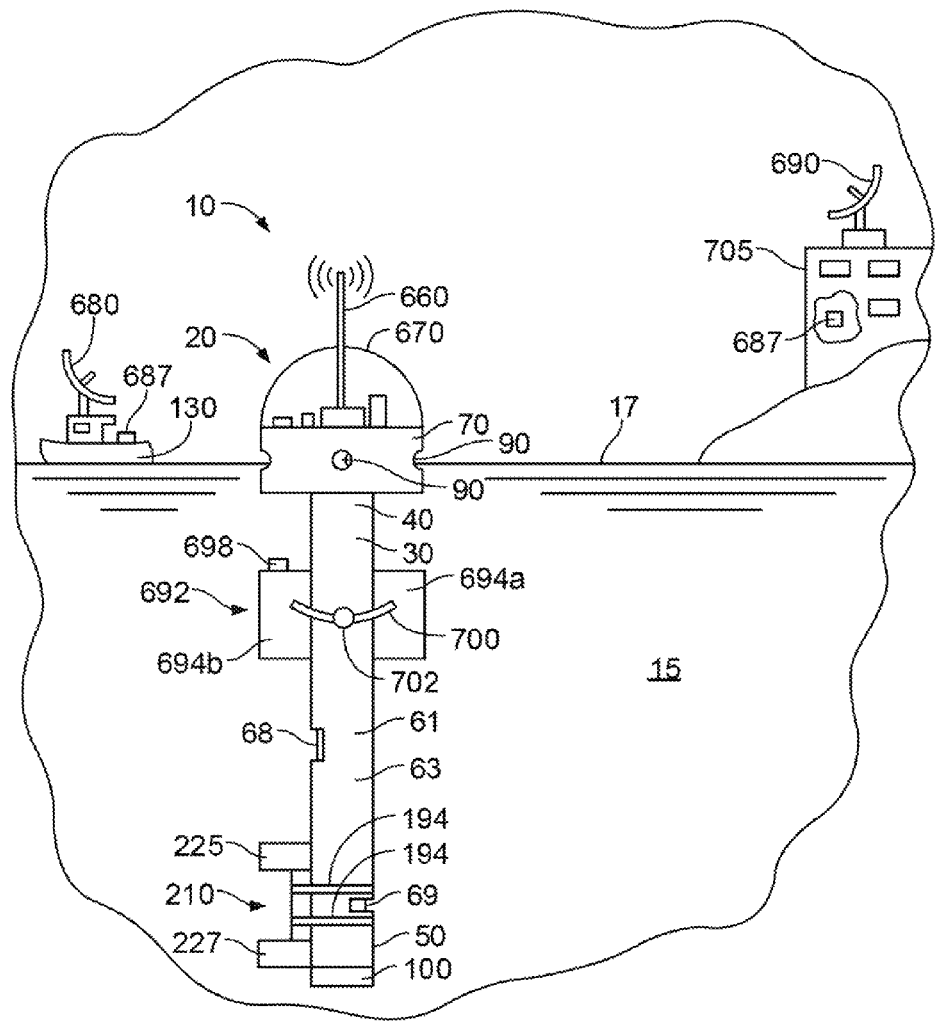
FIG. 2 is a diagram illustrating a cut-away side view of an autonomous biobuoy system, as deployed by a boat, as known in the prior art and capable of implementing an embodiment of the present disclosure.
Figure 3:
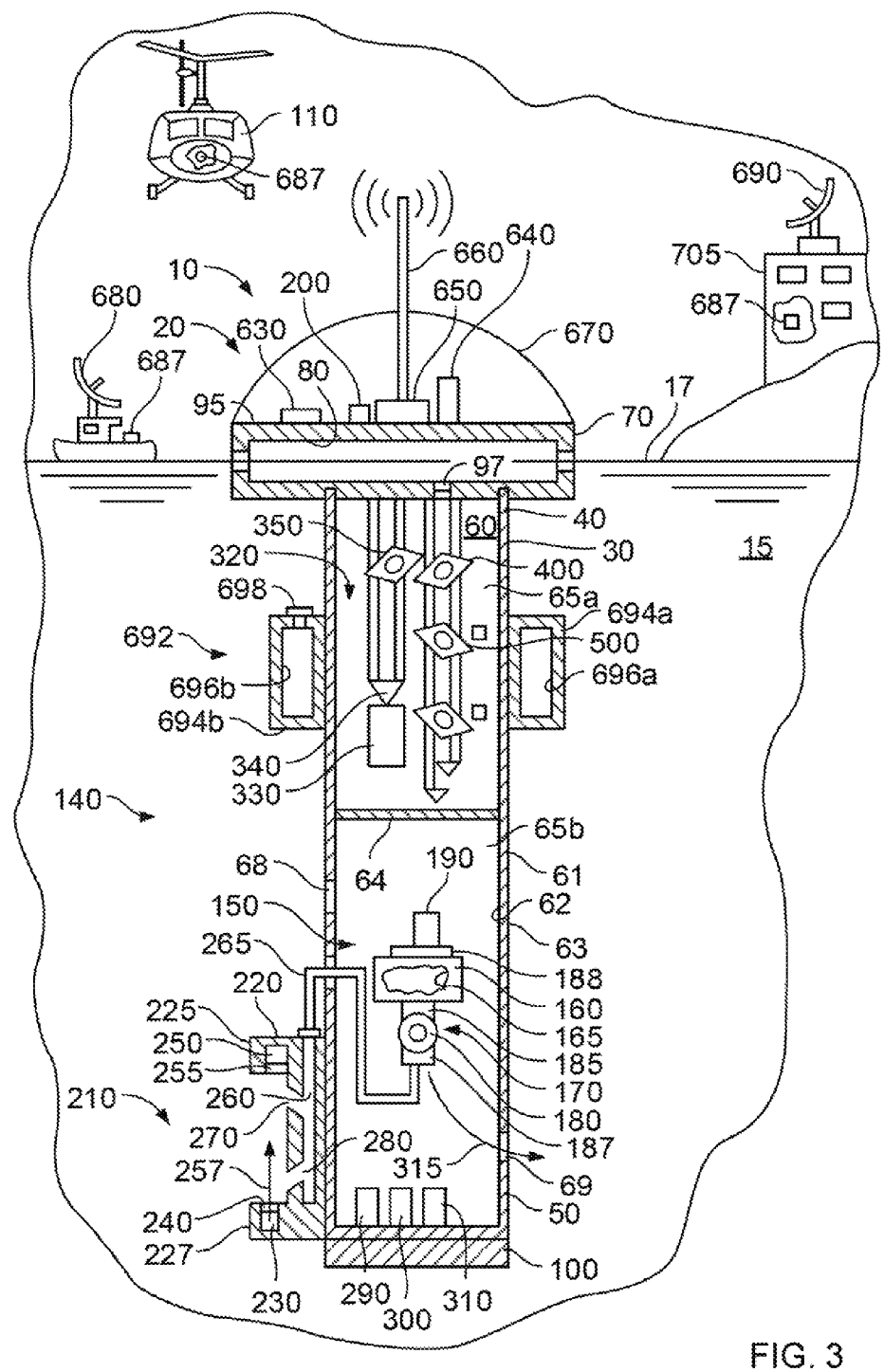
FIG. 3 is a diagram illustrating a cut-away side view of an autonomous biobuoy system, as deployed by a helicopter, as known in the prior art and capable of implementing an embodiment of the present disclosure.
Figure 4:
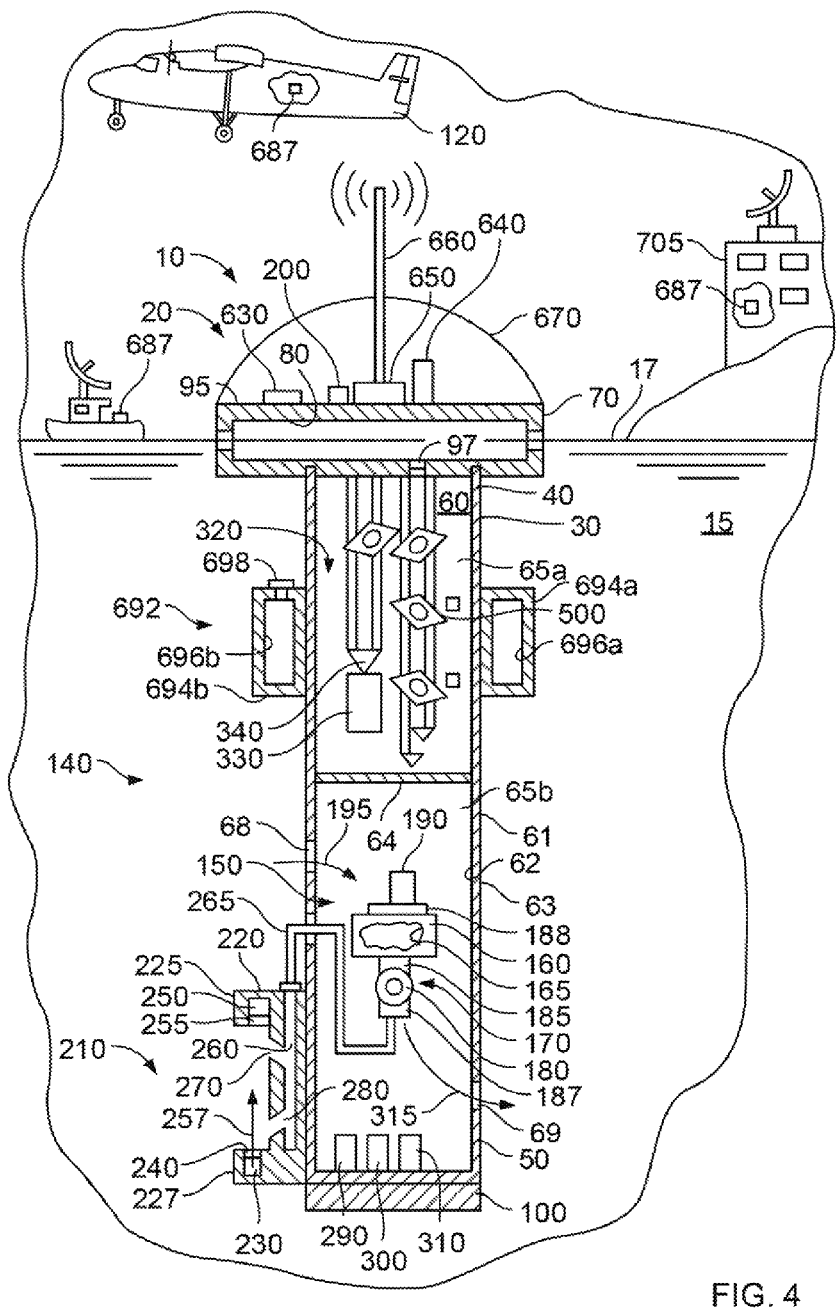
FIG. 4 is a diagram illustrating a cut-away side view of an autonomous biobuoy system, as deployed by an airplane, as known in the prior art and capable of implementing an embodiment of the present disclosure.
Figure 5:
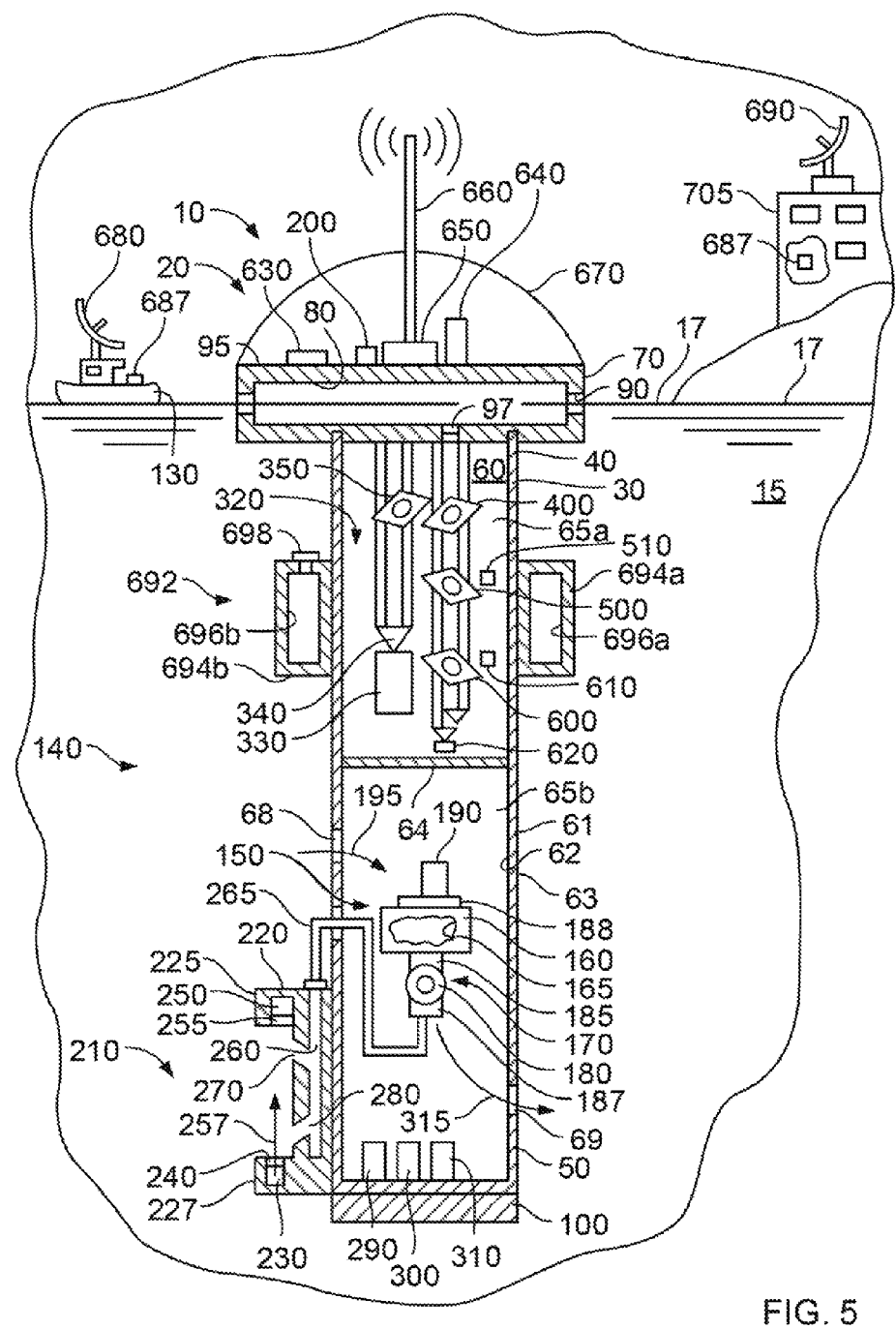
FIG. 5 is a diagram illustrating a cut-away side view of an autonomous biobuoy system, as deployed by a boat, as shown in FIG. 2, as known in the prior art and capable of implementing an embodiment of the present disclosure.

Referring to FIG. 5, this diagram illustrates, in a cut-away side view, an autonomous biobuoy system 10, as deployed by a boat 130, as shown in FIG. 2. The system 10 comprises a test assembly 320 disposed in a tubular member 30, for example, in accordance with aspects in an embodiment of the present disclosure. Still referring to FIG. 5 and referring ahead to FIG. 6, together, the POL detector assembly 320 is configured to detect petroleum, oil, and lubricant contaminants that tend to float near, or on, the surface 17 of the marine environment 15. The POL detector assembly 320 comprises an illumination source, such as a lamp 330 coupled with the electronics unit 200, e.g., by a wire (not shown), the electronics unit 200 controlling the operation of the lamp 330. A light beam from the lamp 330 is transmitted through a collimating lens 340 along a first light path 345, and the collimating lens 340 is aligned with the lamp 330, wherein the collimating lens 340 reduces divergence of the light beam, whereby light rays from the lamp 330 remain parallel. The collimated light beam is received by a first dichroic mirror 190 aligned with collimating lens 340. The first dichroic mirror 350 selectively reflects the light in the light beam according to wavelengths present in the light beam.

Figure 6:
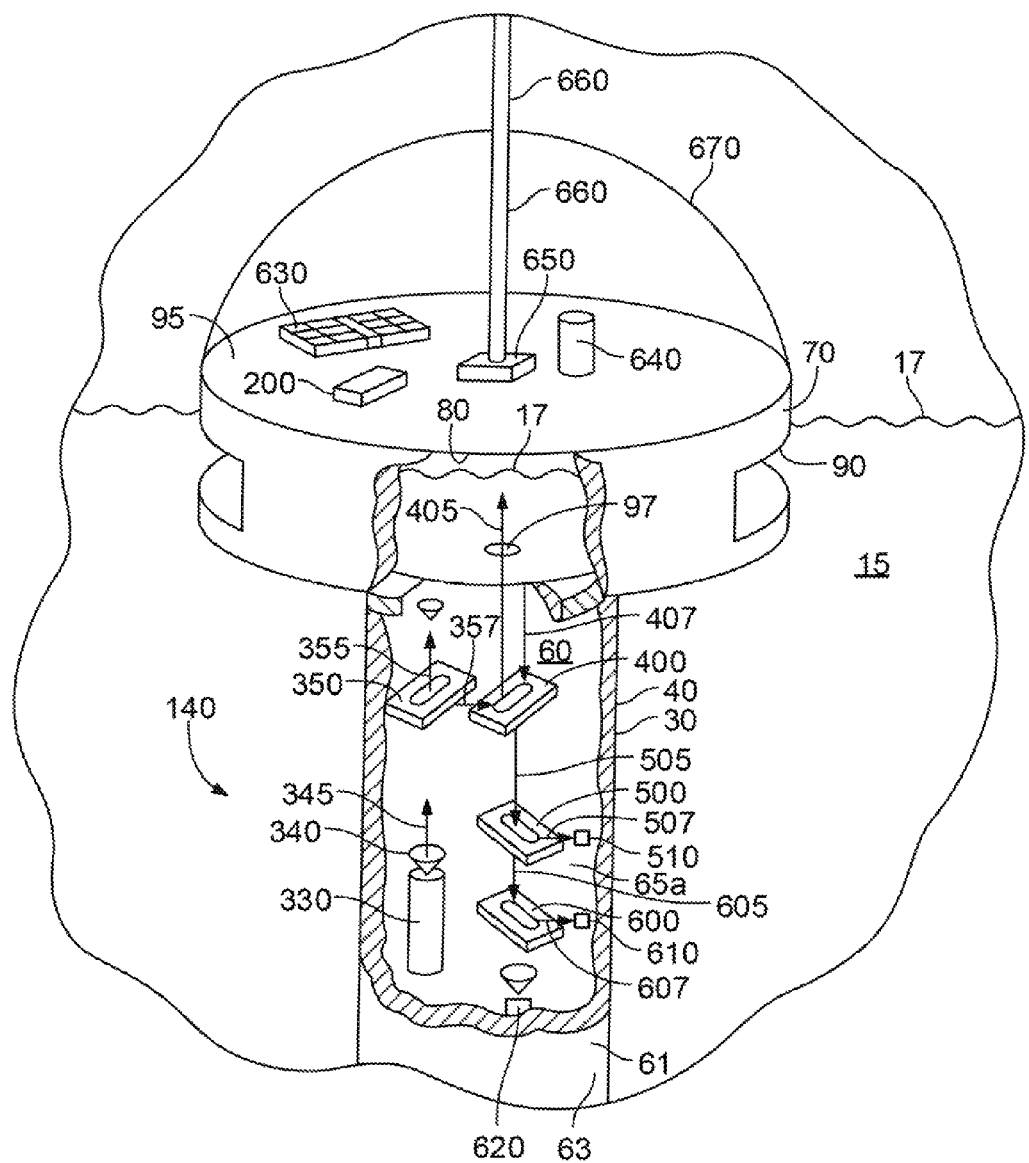
FIG. 6 is a diagram illustrating a cut-away perspective view of an autonomous biobuoy system, as known in the prior art and capable of implementing an embodiment of the present disclosure.

Still referring to FIG. 5 and referring ahead to FIG. 6, depending on the wavelengths in the light beam, e.g., a first light beam, the first dichroic mirror 350 splits the first light beam into a second light beam along a second light path 355 and a third light beam along a third light path 357. The second light beam along the second light path 355 travels through the first dichroic mirror 350, while the third light beam along the third light path 357 is reflected at a right angle to the second light path 355. The third light beam along the third light path 357 is received by a second dichroic mirror 400. As the third light beam along third light path 357 is received by the second dichroic mirror 400, the third light beam is reflected at a right angle as a fourth light beam along a fourth light path 405 travels through the optical window 97 aligned with the second dichroic mirror 400. As the fourth light beam passes through the optical window 97, the fourth light beam will illuminate fluid in the chamber 80 defined by the cap 70. The light that enters the chamber 80 is back-scattered, or reflected, by particles present in the fluid therein. Such particles may result from petroleum, oil, or lubricants near, or on, the surface 17 of the marine environment 15. Some of this back-scattered, or reflected, light passes through the optical window 97 as a fifth light beam along a fifth light path 407, wherein the light is received by the second dichroic mirror 400 and passes there through. The light beam passing through optical window 97 contains a plurality of wavelengths.

Still referring to FIG. 5 and referring ahead to FIG. 6, the light passing through second dichroic mirror 400 along the light path 407 is received by a third dichroic mirror 500 aligned with the second dichroic mirror 400. The light received by third dichroic mirror 500 is split into two light beams according to the wavelengths of the light that is reflected back through the optical window 97 along fifth light path 407. A first one of these light beams passes along a sixth light path 505 and through a third dichroic mirror 500 while a second one of these light beams is reflected at a right angle along a seventh light path 507. The light traveling along the seventh light path 507 is received by a first photo detector channel 510 for detecting a first one of the wavelengths in the light beam originating from optical window 97. Light traveling along the sixth light path 505 that passes through the third dichroic mirror 500 is received by a fourth dichroic mirror 600.

Still referring to FIG. 5 and referring ahead to FIG. 6, the light received by the fourth dichroic mirror 600 is also split into two light beams. A first one of these light beams passes through the fourth dichroic mirror 600 along an eighth light path 605 while a second one of these light beams is reflected at a right angle along a ninth light path 607. The light traveling along the ninth light path 607 is received by a second photodetector channel 610 for detecting a second one of the wavelengths in the light beam originating from optical window 97. Light that travels along the eighth light path 605 and that passes through the fourth dichroic mirror 600 is received by a third photodetector channel 620 for detecting a third one of the wavelengths in the light beam originating from optical window 97. Data from photodetector channels 510, 610, 620 indicate types of petroleum, oil, and lubricants present near, or on, the surface 17 of the marine environment 15.

Still referring to FIG. 5 and referring ahead to FIG. 6, the second dichroic mirror 400, the third dichroic mirror 500, and the fourth dichroic mirror 600 separate light from the optical window 97 into three spectral bands or wavelengths. These spectral bands are subject to multispectral analysis for discriminating between different contaminants located near, or on, the surface 17. The three separate wavelengths of light reflected by the second dichroic mirror 400, the third dichroic mirror 500, and the fourth dichroic mirror 600 are respectively detected by the first photodetector channel 510, the second photodetector channel 610, and the third photodetector channel 620. Each of the first photodetector channel 510, the second photodetector channel 610, and the third photodetector channel 620 are coupled with the electronics unit 200, e.g., by way of electrical conduits (not shown). The first compartment 65a is fluid-tight to prevent fluid that is entering the intake port 68 from contacting the POL detector assembly 320, whereby the detector assembly 320 specifically tests for a presence of at least one of petroleum, oil, and lubricant near, or on, the surface 17 of the marine environment 15.

Referring to FIG. 6, this diagram illustrates, in a cut-away perspective view, an autonomous biobuoy system 10, with some parts removed for clarity, wherein a petroleum, oil, and lubricant (POL) detector assembly 320 is disposed in a tubular member 30, in accordance with aspects in an embodiment of the present disclosure. The system 10 further comprises: a solar panel 630 disposed on the platform 95 of the cap 70 for powering the detector assembly 140, the electronics unit 200, the transmissometer assembly 210, the first photodetector channel 510, the second photodetector channel 610, the thermistor 290, the conductivity detector 300, the depth detector 310, the POL detector assembly 320, the lamp 330, and the third photodetector channel 620. The solar panel 630 is also coupled with, and powers, a global positioning system (GPS) unit 640. The GPS unit 640, disposed on the platform 95, identifies a location of the housing 20 as disposed in the marine environment 15. Each of the foregoing components generates an electrical output signal that is received by electronics unit 200, wherein an electrical output signal is received and transformed (processed) by the electronics unit 200 into a data signal appropriate for radio frequency transmission.

Still referring to FIG. 6, the system 10 further comprises a first radio frequency transmitter-receiver 650 disposed on the platform 95 and coupled with the electronics unit 200, e.g., by an electrical cable. The radio frequency transmitter-receiver 650 comprises a transmitter 652 and a receiver 654, as shown in FIG. 1, and is also coupled with, and powered by, the solar panel 630. The radio frequency transmitter-receiver 650 is configured to receive the output signal from the electronics unit 200, which in turn, receives the output signals from the detector assembly 140, the transmissometer assembly 210, the first photodetector channel 510, the second photodetector channel 610, the thermistor 290, the conductivity detector 300, the depth detector 310, the POL detector assembly 320, the lamp 330, the third photodetector channel 620, and the GPS unit 640. The transmitter-receiver 650 transmits or broadcasts the output signals received from the electronics unit 200 through an antenna 660 coupled therewith. A transparent or translucent dome 670 is mounted on the platform 95 via a seal therebetween, thereby enclosing the solar panel 630, the electronics unit 200, the GPS unit 640, and the transmitter-receiver 650. The dome 670 is transparent so that these components are available for visual inspection before deployment or after retrieval of the housing 20 from the marine environment 15. The dome 670 comprises a clear plastic material. Enclosing these components within the dome 670 shields or protects these components from debris damage or corrosion, e.g., due to salt, from the marine environment 15.

Still referring to FIG. 6 and referring back to FIGS. 1 and 5, the system 10 further comprises: a data acquisition and control unit 675 for receiving a signal broadcast through the antenna 660, the data acquisition and control unit 675 which comprises a first radio frequency receiver-transmitter 680 disposed aboard at least one of the boat 130, the helicopter 110, and the airplane 120. The first radio frequency receiver-transmitter 680, in turn, transmits or broadcasts the signal to an Internet web address 685 for retrieval by at least one remote computer 687 having authorized access thereto. Alternatively, the signal broadcast through antenna 660 is received by a second radio frequency receiver-transmitter 690 disposed in a land-based facility 705. The at least one remote computer 687 is disposed on at least one of the boat 130, the helicopter 110, the airplane 120, and the land-based facility 705.

Still referring to FIG. 6 and referring back to FIGS. 1, 2 and 3, the system 10 further comprises an adjustable ballast 692 for controlling vertical movement of the housing 20, e.g., to controllably and vertically descend as well as controllably and vertically ascend, in relation to the marine environment 15. The adjustable ballast 692 controls buoyancy of biobuoy system 10 while disposed in the marine environment 15. The adjustable ballast 692 comprises a first ballast tank 694a coupled with the outer wall 63 of the tubular member 30. The first ballast tank 694a defines a leak-tight first chamber 696a therein. Also, a second ballast tank 694b is coupled with outer wall 63 of tubular member 30. The second ballast tank 694b also defines a leak-tight second chamber 696b therein and includes an electrically operable valve, such as a two-way valve 698, in communication with second chamber 696b. A conduit 700, having an electrically operable flow valve 702 disposed therein, interconnects the first chamber 696a and the second chamber 696b.

Still referring to FIG. 6 and referring back to FIGS. 1, 2 and 3, prior to deployment of the biobuoy system 10, the first chamber 696a is filled with a predetermined amount of pressurized gas, such as air. During deployment of biobuoy system 10 in the marine environment 15, the housing 20 may be caused, if desired, to vertically descend to a predetermined depth in the marine environment 15 for testing characteristics, e.g., a presence of bioluminescent organisms, therein. When deployed in the marine environment 15, the housing 20 tends to float by buoyancy of the cap 70 having a specific gravity less than the specific gravity of the marine environment 15. When desired, the housing 20 is sinkable in the marine environment 15 for measuring characteristics at predetermined depths of the marine environment 15. In this regard, the valve 698 may be opened to allow fluid to enter the second tank 694b, thereby decreasing buoyancy of housing 20. The relatively dense gas in the first ballast tank 694a is in combination with the presence of the ballast member 100.

Still referring to FIG. 6 but also referring back to FIGS. 1, 2 and 3, descent of the housing 20 is controlled by operating the flow valve 702, thereby releasing gas, in a metered manner, from the first ballast tank 694a through the conduit 700 and into the second ballast tank 694b. As the gas enters an empty second ballast tank 694a, the gas tends to expand, thereby adding buoyancy to the housing 20, and thereby slowing, or stopping, vertical descent of the housing 20 into the marine environment 15. The valve 698 is operable during this time for releasing the gas in the second ballast tank 694b, thereby adding further buoyancy, and thereby vertically raising the housing 20 in the marine environment 15. Operation of the adjustable ballast 692 is controlled by the electronics unit 200. After the housing 20 resurfaces at the surface 17, the transmitter-receiver 650 transmits the test data to the data acquisition and control unit 675. The adjustable ballast 692 is coupled with the electronics unit 200, e.g., by electrical wires or cables (not shown). Moreover, the cap 70 has a specific gravity less than 1000 kg/m$^3$ and, thus, adds even more buoyancy to the housing 20.

Figure 7:
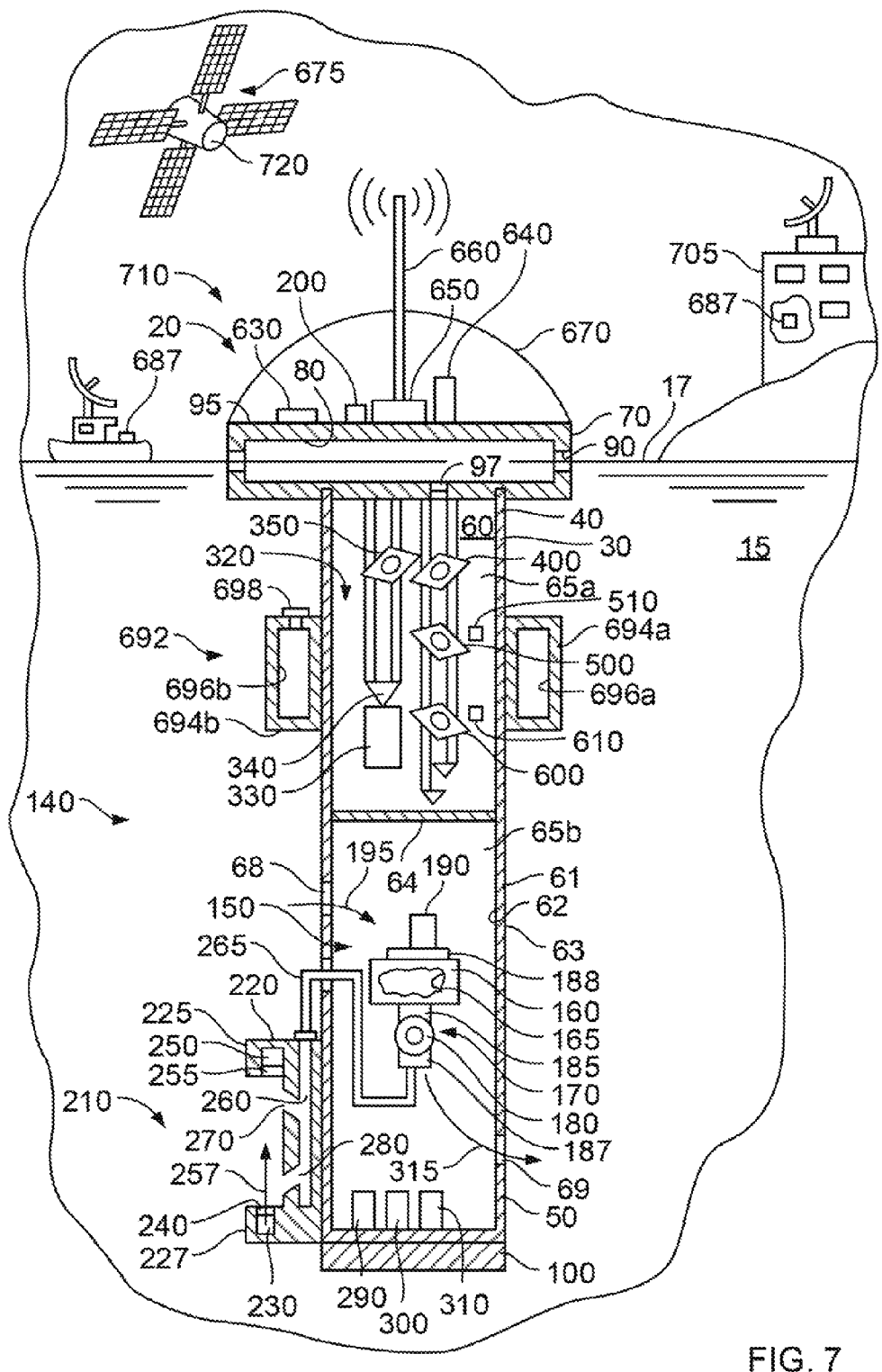
FIG. 7 is a diagram illustrating a cut-away side view of an autonomous biobuoy system, as deployed by a boat, as shown in FIG. 2, where the system is configured to communicate with a satellite, as known in the prior art and capable of implementing an embodiment of the present disclosure.

Referring to FIG. 7, this diagram illustrates, in a cut-away side view, an autonomous biobuoy system 710 as deployed by a boat 130, as shown in FIG. 2, where the system 710 is configured to communicate with a satellite 675, for example, in accordance with aspects in an embodiment of the present disclosure. The autonomous biobuoy system 710 is configured to detect at least one characteristic of the marine environment 15. According to this embodiment of the autonomous biobuoy system 710, the signal broadcast trough antenna 660 is received by an overhead satellite 720. The overhead satellite 720, in turn, relays the data signal to the Internet web address 685 for retrieval and further analysis by the remote computer 687. A satellite 720 is selectable, such that the satellite 720 is in one of a near-polar orbit, a sun synchronous orbit, and geosynchronous orbit, as required by a geographic location of the housing 20.

Figure 8:
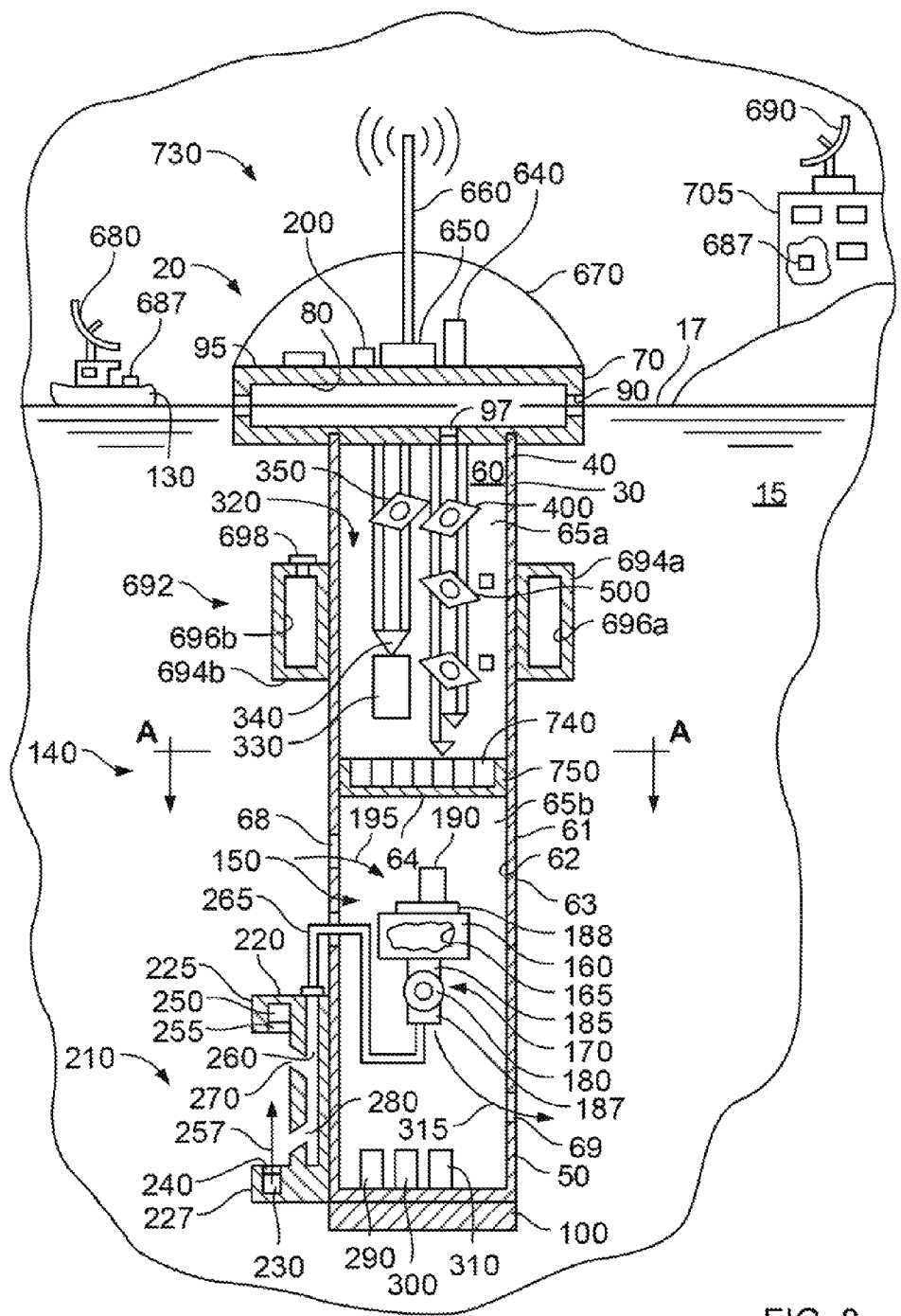
FIG. 8 is a diagram illustrating a cut-away side view of an autonomous biobuoy system, as deployed by a boat, as shown in FIG. 2, as known in the prior art and capable of implementing an embodiment of the present disclosure.
Figure 9:
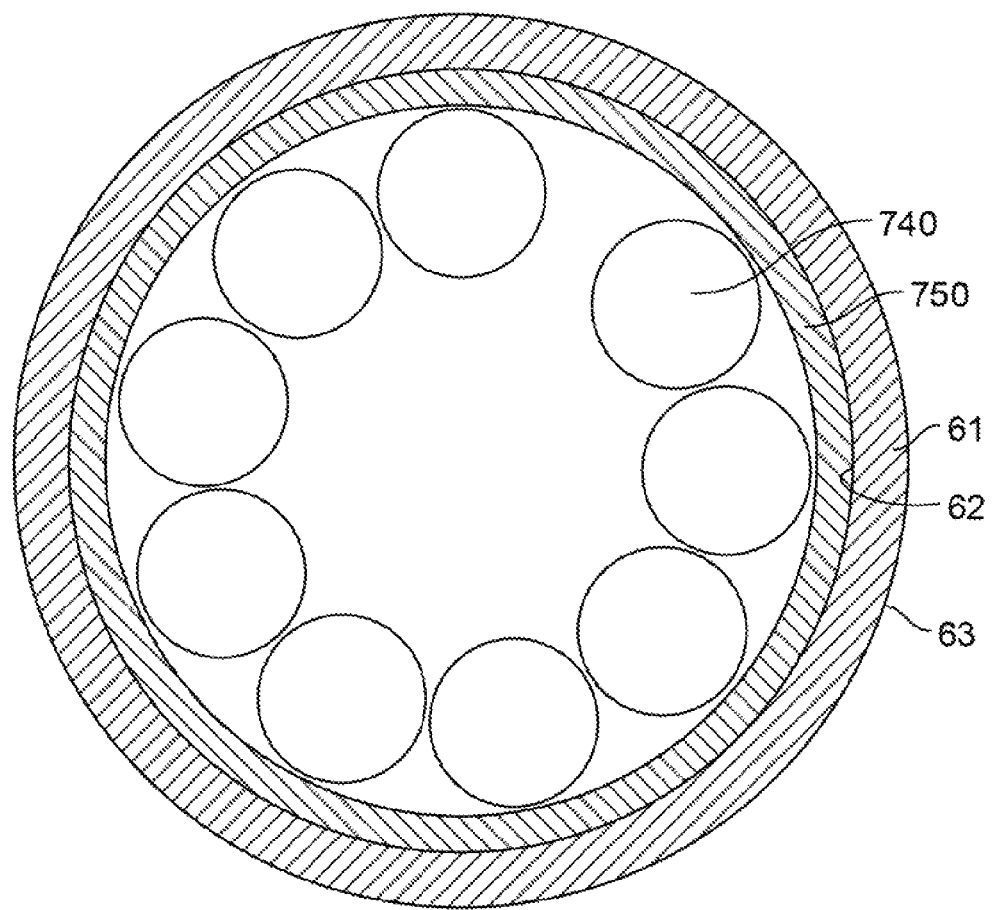
FIG. 9 is a diagram illustrating a cross-sectional view of an autonomous biobuoy system, as shown in FIG. 8, the system comprising a tubular member for accommodating a variety of components, in accordance with aspects in an embodiment of the present disclosure.

Referring to FIGS. 8 and 9, together, the autonomous biobuoy system 730 is configured to detect at least one characteristic of the marine environment 15. In FIG. 8, this diagram illustrates, in a cut-away side view, an autonomous biobuoy system 730 as deployed by a boat 130, as shown in FIG. 2, the system 730 comprising a battery arrangement, such as a battery belt 750, disposed in a tubular member 30 for powering thereby, for example, in accordance with aspects in an embodiment of the present disclosure. In FIG. 9, this diagram illustrates, in a cross-sectional view, an autonomous biobuoy system 730 along section A-A, as shown in FIG. 8, and the system 730 comprises a tubular member 30 for accommodating a variety of components, in accordance with aspects in an embodiment of the present disclosure. According to this third embodiment of the biobuoy system 730, a battery arrangement, which comprises a plurality of batteries 740 coupled with interior surface 62 of tubular member 30, is disposed in the fluid-tight first compartment 65a of tubular member 30. The batteries 740 are coupled with, and power, the detector assembly 140, the electronics unit 200, the transmissometer assembly 210, the first photodetector channel 510, the second photodetector channel 610, the thermistor 290, the conductivity detector 300, the depth detector 310, the POL detector assembly 320, the lamp 330, the third photodetector channel 620, and the GPS unit 640.

Still referring to FIGS. 8 and 9 together, each of the batteries 740 may reside in respective ones of a plurality of pockets (not shown) defined by a battery belt 750 that is coupled with the interior surface 62. The batteries 740 enable operation of the biobuoy system 730 without the need for the solar panel 630, otherwise powering the biobuoy system 730. The biobuoy system 730 is also configurable for use during extended periods of time in regions where sunlight is absent or nearly absent, such as regions of northern Europe, e.g., Finland and the like, during winter, at the North Pole, or after the September Equinox. Thus, the biobuoy system 730 is conveniently operable without use of the solar panel 630.

Figure 10:
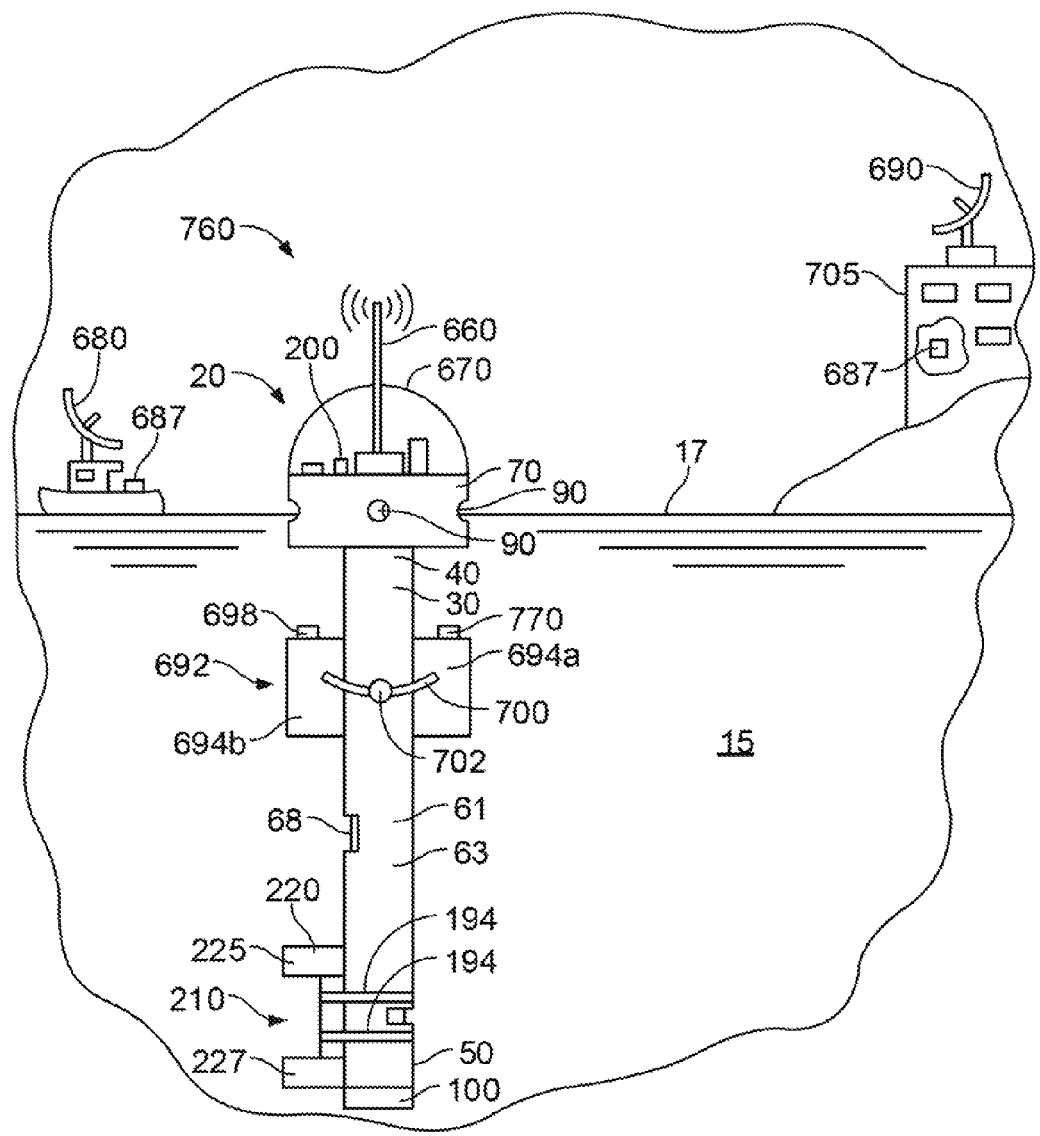
FIG. 10 is a diagram illustrating a side view of an autonomous biobuoy system, as deployed by a boat, as known in the prior art and capable of implementing an embodiment of the present disclosure.
Figure 11:
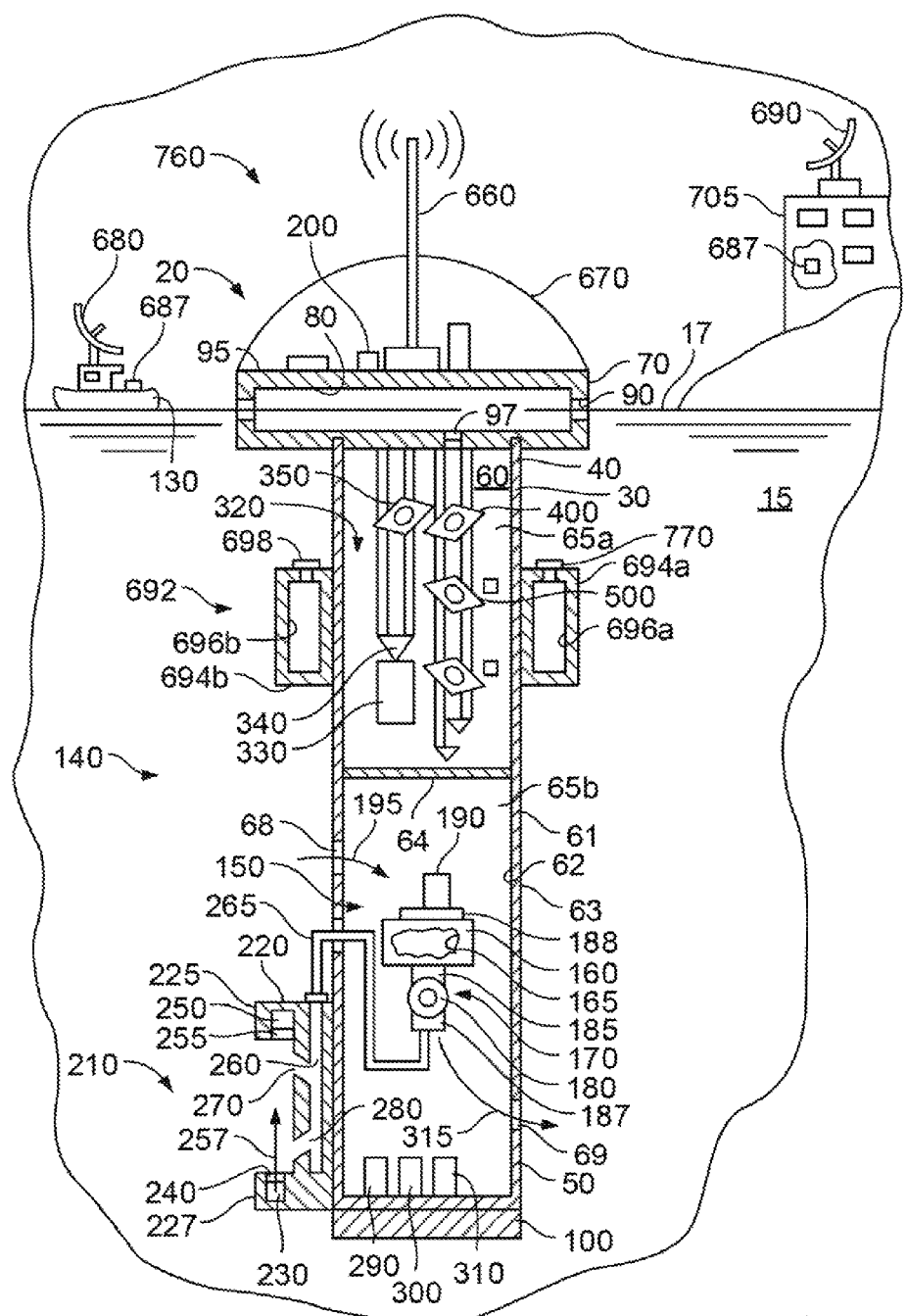
FIG. 11 is a diagram illustrating a cut-away side view of an autonomous biobuoy system, as deployed by a boat, as known in the prior art and capable of implementing an embodiment of the present disclosure.

Referring to FIGS. 10 and 11, together, an autonomous biobuoy system 760 is configured to detect at least one characteristic of the marine environment 15. In FIG. 10, this diagram illustrates, in aside view, an autonomous biobuoy system 760 as deployed by a boat 130, as shown in FIG. 2, where the system 760 comprises a feature for scuttling, such as a scuttling valve 770, thereby, in accordance with aspects in an embodiment of the present disclosure. In FIG. 11, this diagram illustrates, in a cut-away side view, an autonomous biobuoy system 760, as shown in FIG. 10, as deployed by a boat 130, as shown in FIG. 2, in accordance with aspects in an embodiment of the present disclosure.

Still referring to FIGS. 10 and 11, together, the biobuoy system 760 comprises a scuttling valve 770 for scuttling thereby, wherein the valve 770 is in communication with the first chamber 696a, such that, as the valve 770 is opened, fluid from the marine environment 15 enters the first chamber 696a. Also, the two-way valve 698 is opened in a manner that allows fluid from the marine environment 15 to enter the second chamber 696b. The added mass provided by fluid in the first chamber 696a and the second chamber 697b sinks the housing 20 in the marine environment 15. The valves 698, 770 are coupled with, and controllable by, the electronics unit 200. In addition, the ballast 100 facilitates sinking the housing 20 into the marine environment 15. In this manner, the ballast 100 serves a dual purpose: firstly, to facilitate stabilizing a motion of the housing 20 in the marine environment 15; and, secondly, to facilitate scuttling the housing 20.

Still referring to FIGS. 10 and 11, together, and referring back to FIGS. 1-9, the systems 10, 710, 730, 760 are autonomously operable, such as by way of an on-board power source, e.g., by at least one of the solar panel 630 and the batteries 740, rather than by an external power source, such as an electrical cable coupled with a power source of a boat. Also, the systems 10, 710, 730, 760 are configured to transmit detection data and receive operating instructions by way of radio frequency transmission, rather than by way of a data transmission cable. Thus, the systems 10, 710, 730, 760 need not be tethered, such as by a cable, to an external power source or data transmission feature. In other words, the systems 10, 710, 730, 760 need not be tethered, such as by way of a power cable or a data transmission cable, to a boat, an aerial vehicle, or a land-based facility in order to obtain power or to receive and transmit detector data. For example, the systems 10, 710, 730, 760 may float with ocean currents for extended periods of time while detecting and transmitting characteristics of the ocean environment.

Figure 12:
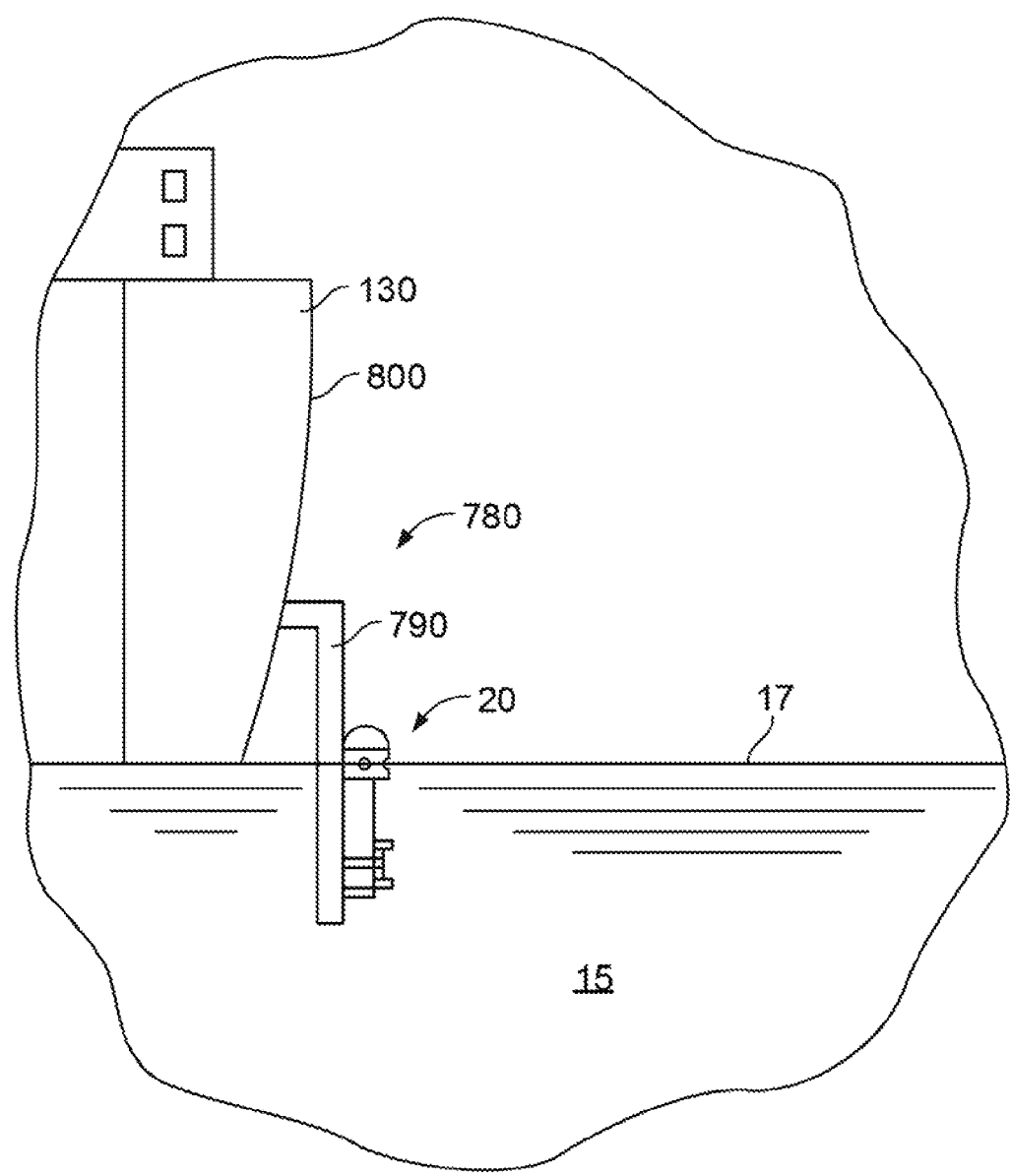
FIG. 12 is a diagram illustrating a side view of an autonomous biobuoy system, as deployed by a boat, as known in the prior art and capable of implementing an embodiment of the present disclosure.

Referring to FIG. 12, this diagram illustrates, in a side view, an autonomous biobuoy system 780 as deployed by a boat 130, as shown in FIG. 2, where the system 780 is removably coupled with a hull 800 of the boat 130, for example, in accordance with aspects in an embodiment of the present disclosure. The system 780 is configured to detect at least one characteristic of the marine environment 15. In the system 780, the housing 20 is attached, such as by a bracket 790, to the hull 800 of the boat 130. This system 780 provides an alternative technique for detecting the at least one characteristic of the marine environment 15 and for transmitting at least one signal corresponding to the at least one characteristic by radio frequency transmission. In this sense, the system 780 is autonomous for at least that the power supply and the data transmission involve radio frequency transmission rather than by tethered cable.

Still referring to FIG. 12 and referring back to FIGS. 1-11, the detector assembly 140 detects at least one characteristic of the marine environment 15 and provides that data corresponding to the at least one characteristic to the transmitter 652, e.g., via the electronics unit 200. The transmitter 652, in turn, transmits such data by radio frequency transmission to the data acquisition and control unit 675. The data acquisition control unit 675 avails the data to an Internet web address 685 by way of radio frequency transmission, wherein a remote computer 687 accesses the data. In addition, the remote computer 687 may send operational instructions to the system, such as the system 780, by sending the instructions to the Internet web address 685, wherein the data acquisition and control unit access the instructions. The data acquisition and control unit 675 then transmits a signal to the receiver 654 for operating adjustable ballast 692.

Still referring to FIG. 12 and referring back to FIGS. 1-11, by way of example only, during operation of the systems 10, 710, 730, 760, 780, the light-sensitive detector 190 is powered for approximately four (4) seconds before the pump 180 is activated for a sampling period of approximately ten (10) seconds. During the sampling period, bioluminescence is quantified and averaged. As the pump 180 is deactivated, a percentage transmission of the fluid clarity is measured. The raw data are then sent, via radio frequency transmission, to the receiver-transmitter 680 or the receiver-transmitter 690. The data are then automatically processed and posted to a real-time web address, such as the Internet web address 685, via a satellite link, if desired.

Referring back to FIGS. 1-12, for example, a suitable camera may be mounted on tubular member 30 for visually recording events near or in the biosphere, such as the presence of sources that may be stimulating bioluminescent activity. As yet another example, any of the various embodiments of the biobuoy systems described herein may be tethered to a deployment vessel, such as the boat 130, an aerial deployment vehicle, such as the helicopter 110 or the airplane 120, for deployment in the marine environment 15 and for maintaining the biobuoy system at a predetermined location within the marine environment 15. As a further example, photodiodes may be used, rather than photodetectors, e.g., to lower cost of assembly and to make the biobuoy system expendable, e.g., by scuttling the biobuoy system, with less cost impact.

Figure 13:
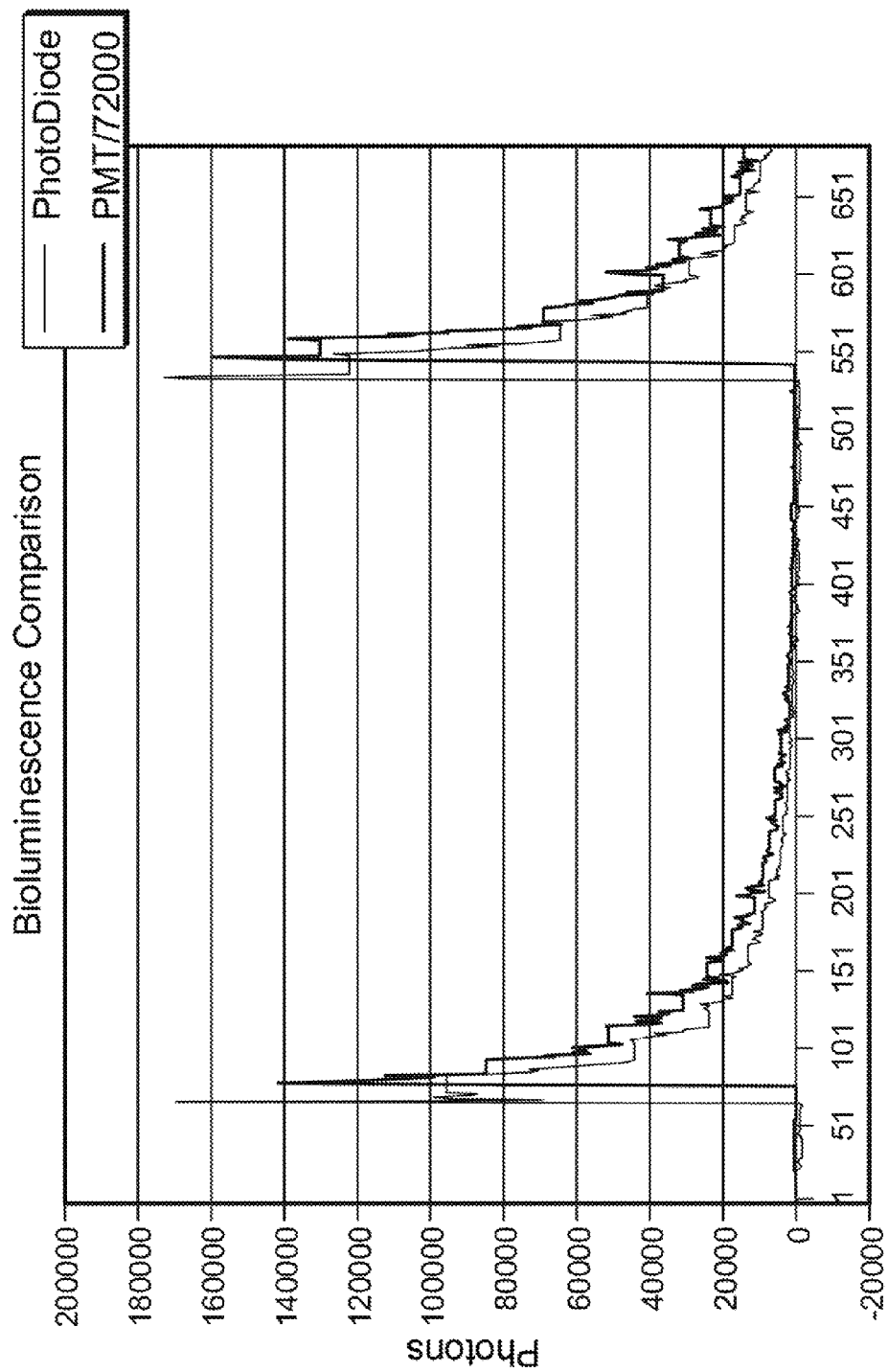
FIG. 13 is a graph illustrating data relating to detection of at least one characteristic of a marine environment by way of an autonomous biobuoy system, the system comprising a detector assembly configured to detect bioluminescence, in accordance with aspects in an embodiment of the present disclosure.

Referring to FIG. 13, this graph illustrates data relating to the detection of at least one characteristic of a marine environment 15 by way of an autonomous biobuoy system S, having many of the components described in relation to the systems 10, 710, 730, 760, 780, wherein the system S comprises at least one detector assembly 140 that is responsive to bioluminescence, in accordance with aspects in an embodiment of the present disclosure. Instead of using a photomultiplier, the at least one detector assembly 140 alternatively comprises a single photodiode 141 configured to measure bioluminescence, as demonstrated by the graph of FIG. 13.

Figure 14:
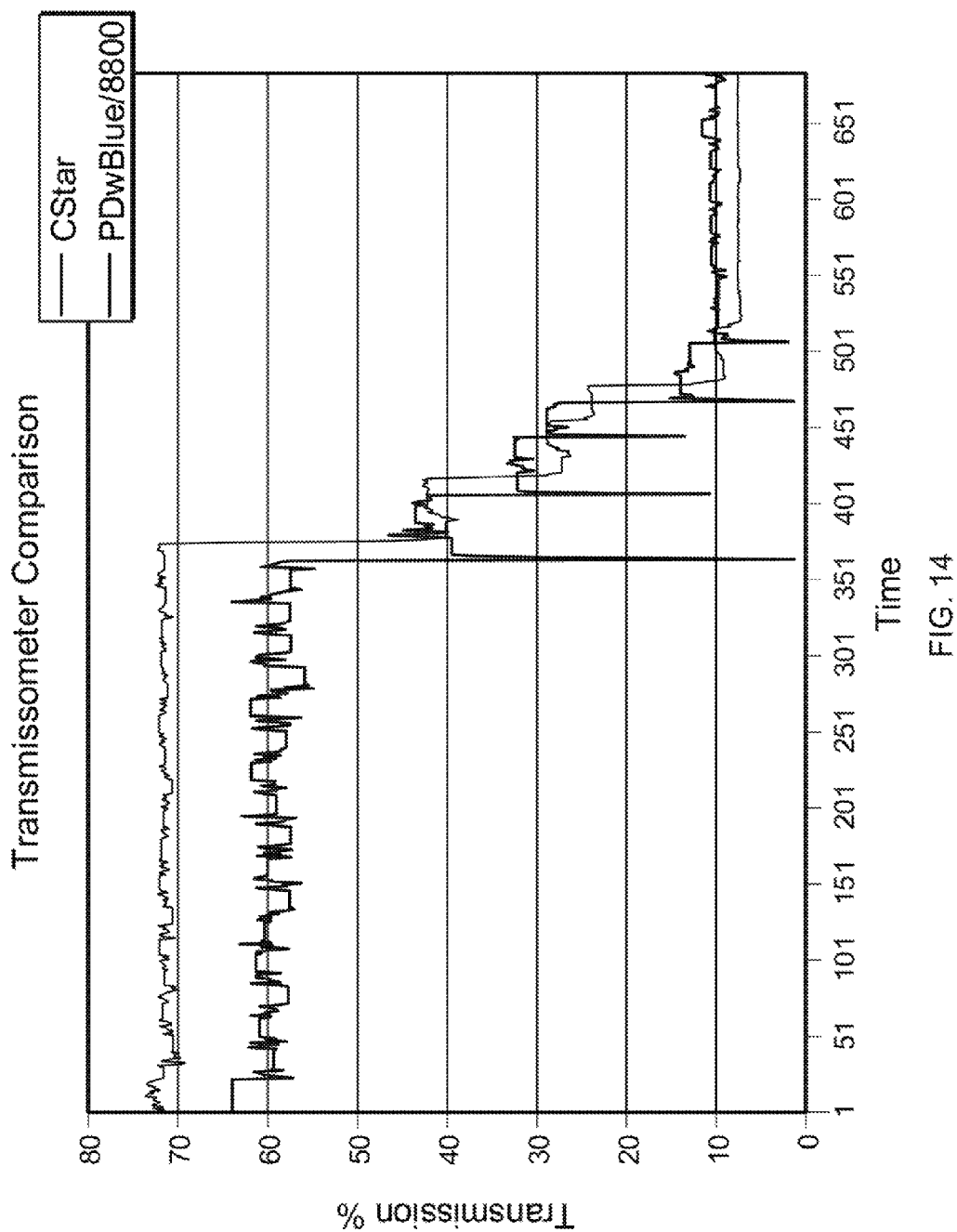
FIG. 14 is a graph illustrating data relating to detection of at least one characteristic of a marine environment by way of an autonomous biobuoy system, the system comprising a detector assembly configured to detect both bioluminescence and transmissivity, in accordance with an embodiment of the present disclosure.

Referring to FIG. 14, this graph illustrates data relating to transmission or transmissivity data, such as at least one detector assembly output signal, that is received and transmitted by the at least one detector assembly 140 of an autonomous biobuoy system S, having many of the components described in relation to the systems 10, 710, 730, 760, 780 comprising at least one photodetector assembly 140, the assembly 140 comprising a single photodiode 141 configured to function as a transmissometer, in accordance with an embodiment of the present disclosure. Instead of using a photomultiplier, the at least one detector assembly 140 alternatively comprises the single photodiode 141 configured to measure both bioluminescence as well as transmissivity in response to a light source L comprising a blue light emitting diode (FIG. 15), as demonstrated by the graph of FIG. 14. The marine environment 15 comprises any body of water; and the autonomous biobuoy system S is configured to autonomously conduct extended duration marine studies of bioluminescence and to quantify bioluminescence over time and with respect to fluid temperature and fluid clarity for determining seasonal variation in levels of toxicity in the marine environment.

Figure 15:
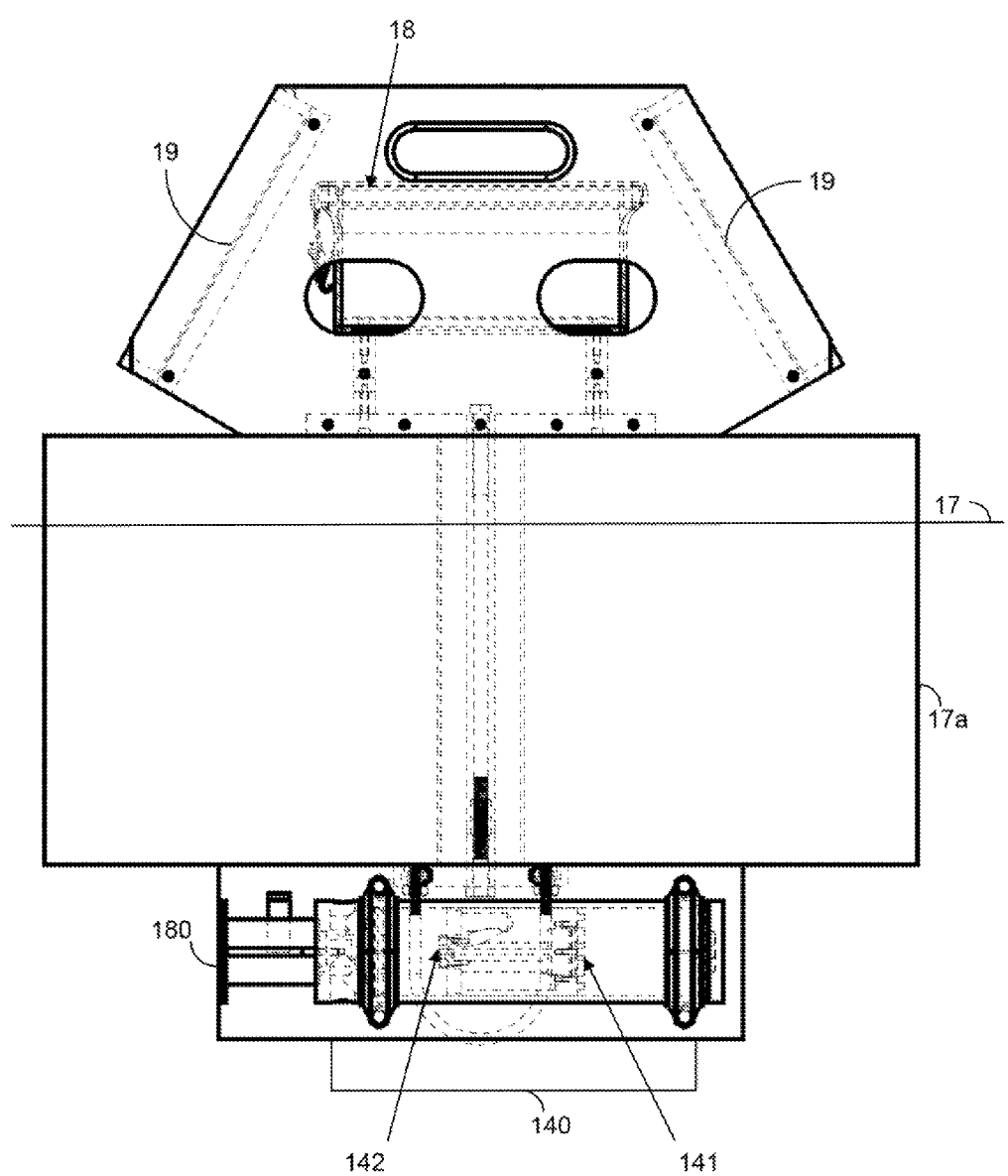
FIG. 15 is a diagram illustrating an autonomous biobuoy system, in accordance with an embodiment of the present disclosure.

Referring to FIG. 15, an autonomous biobuoy system S for detecting characteristics of a marine environment, the system S comprising: a light source L comprising a blue light emitting diode; a detector assembly 140 for detecting the at least one characteristic of the marine environment, the detector assembly 140 comprising a single photodiode 141 configured to detect stimulated bioluminescence and transmissivity in response to the light source L, where the detector assembly 140 is configured to generate at least one detector assembly output signal responsive to at least one detected characteristic; and a transmitter 652 coupled with the detector assembly 140 for transmitting the at least one detector assembly output signal, in accordance with an embodiment of the present disclosure. By example only, the system S further comprises a pump 180, such as a seawater pump, a float 17a coupled with the detector assembly 140, the float 17a coupled with an environmental enclosure 18, the enclosure 18 accommodating at least one of at least one battery, at least one data logger, at least one modem, and at least one solar charger, wherein the at least one solar charger is coupled with at least one solar panel 19 for powering at least one of the detector assembly 141, the LED 142, and the pump 180.

Still referring to FIG. 15, the system S further comprises: a data acquisition and control unit 675 for receiving a signal broadcast through the antenna 660, where the data acquisition and control unit 675 comprises a first radio frequency receiver-transmitter 680 disposed aboard at least one of the boat 130, the helicopter 110, and the airplane 120. The first radio frequency receiver-transmitter 680, in turn, transmits or broadcasts the signal to an Internet web address 685 for retrieval by at least one remote computer 687 having authorized access thereto. Alternatively, the signal broadcast through antenna 660 is received by a second radio frequency receiver-transmitter 690 disposed in a land-based facility 705. The at least one remote computer 687 is disposed on at least one of the boat 130, the helicopter 110, the airplane 120, and the land-based facility 705.

Still referring to FIG. 15, the alternative autonomous biobuoy system S comprises at least one detector assembly 140, each at least one detector assembly 140 alternatively comprising a single photodiode 141 configured to measure stimulated bioluminescence as well fluid clarity, e.g., by way of light transmission. This autonomous biobuoy system S is further configured to remotely measure bioluminescence, marine fluid clarity, as well as temperature, and this alternative system S is remotely accessible via cellular phone communications, e.g., for at least one of downloading data and uploading data. This alternative system S comprises a size that is smaller than systems 10, 710, 730, 760, 780 as well as smaller than any related art buoys. Further, this alternative system S comprises an electronics unit 200, e.g., an electronic package, eliminating many of the commercial off-the-shelf (COTS) components otherwise used in the related art. The at least one detector assembly 140 comprises a sensor package that facilitates a larger measurement program.

Still referring to FIG. 15, the alternative autonomous biobuoy system S comprises at least one detector assembly 140, each at least one detector assembly 140 alternatively comprising a single light detector, such as a single photodiode 141, configured to measure stimulated bioluminescence as well fluid clarity, e.g., via light transmission. The alternative autonomous biobuoy system S further comprises a plurality of solar panels, such as two solar panels, assisted by a solar charger corresponding to a rechargeable power supply, such as a lithium phosphate iron battery. The rechargeable power supply battery provides power that is sufficient to run a marine fluid bilge pump to pull marine fluid into a light-tight sample chamber to accomplish both the bioluminescence measurement and fluid clarity measurement.

Referring back to FIG. 1, a single photo diode 141, using a blue light emitting diode (LED) as a light source, is configured to measure fluid clarity. Still referring to FIG. 15, the single photodiode 141 comprises a blue light emitting diode (LED) configured to measure fluid clarity. The single photodiode 141 the LED is maskable by a neutral density filter, such as an ND-2 filter, to attenuate the blue light source, thereby preventing saturation of the single photodiode 141. The autonomous biobuoy system S further comprises an environmental enclosure mounted adjacent the plurality of solar panels and an antennae above the fluid line, e.g., the surface 17, for accommodating and protecting the battery, a phone modem, a data logger, and a solar charger. Remote data access to the alternative autonomous biobuoy system S is achievable via at least one phone technology, such as 3G, 4G, 5G, and LTE; and data is at least one of downloadable and uploadable from a remote location having "hot spot" access in relation to the Internet, thereby eliminating a need for satellite communications for downloading the data.

Still referring to FIG. 15, the alternative autonomous biobuoy system S comprises a detector assembly 140, the detector assembly 140 comprising the single photodiode 141 configured to accomplish both measurement goals. Also, the alternative autonomous biobuoy system S further comprises two solar panels assisted by a solar charger corresponding to a rechargeable power supply, such as a lithium phosphate iron battery. The lithium phosphate iron battery powers a marine fluid bilge pump to pull marine fluid into a light-tight sample chamber to accomplish both the bioluminescence measurement and the fluid clarity or transmissivity measurement. The light source L comprises a light emitting diode, such as a blue light emitting diode, for making the fluid clarity measurement. The blue LED is masked by an ND-2 filter to attenuate the blue light source, thereby preventing saturation of the photodiode 141.

Still referring to FIG. 15, satellite communications are not required to download the data as otherwise used in the related art. The cost of the alternative autonomous biobuoy system is greatly reduced over related art instruments because the cost of a photodiode 141 is less than the cost of a photomultiplier tube and the cost of a transmissometer. Further, the alternative autonomous biobuoy system S is more robust for deployment than related art systems. The alternative autonomous biobuoy system S is further reconfigurable for mounting within an autonomous underwater vehicle (not shown), e.g., a submarine, and even for an air-drop deployment for measurements in otherwise inaccessible areas.

Figure 16:
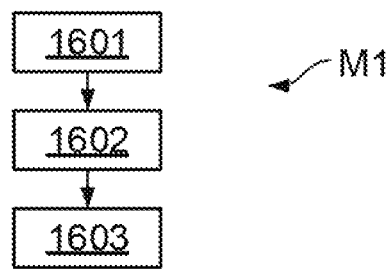
FIG. 16 is a flow diagram illustrating a method of fabricating an autonomous biobuoy system, in accordance with an embodiment of the present disclosure.

Referring to FIG. 16, this flow diagram illustrates a method M1 of fabricating an autonomous biobuoy system S for detecting characteristics of a marine environment 15, as shown in FIG. 15, in accordance with an embodiment of the present disclosure. The method M1 comprises: providing a light source L, providing the light source L comprising providing a blue light emitting diode, as indicated by block 1601; providing a detector assembly 140 for detecting the at least one characteristic of the marine environment 15, providing the detector assembly 140 comprising configuring a single photodiode 141 to detect stimulated bioluminescence and transmissivity in response to the light source L and configuring the detector assembly 140 to generate at least one detector assembly output signal responsive to at least one detected characteristic, as indicated by block 1602; and providing a transmitter, providing the transmitter comprising coupling the transmitter with the detector assembly for transmitting the at least one detector assembly output signal, as indicated by block 1603.

Figure 17:
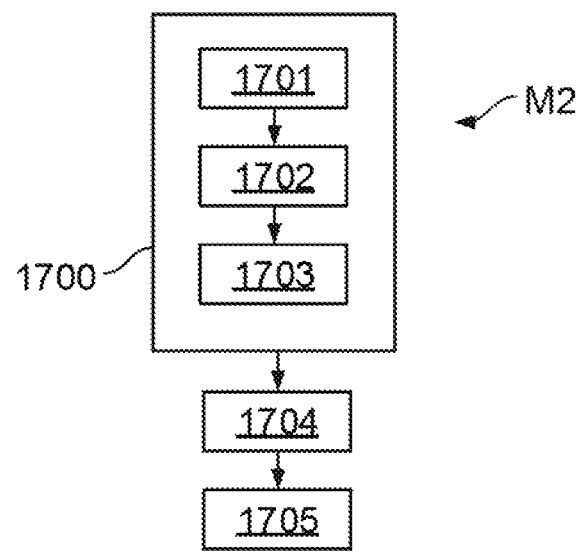
FIG. 17 is a flow diagram illustrating a method of detecting at least one characteristic of a marine environment, such as a marine biosphere, and transmitting at least one detector assembly output signal by way of an autonomous biobuoy, in accordance with an embodiment of the present disclosure.

Referring to FIG. 17, this flow diagram illustrates a method M2 of detecting at least one characteristic of a marine environment 15, such as a marine biosphere, and transmitting at least one detector assembly output signal by way of an S, as shown in FIG. 15, in accordance with an embodiment of the present disclosure. The method M2 comprises: providing an autonomous biobuoy system S, as indicated by block 1700, providing the autonomous biobuoy system S comprising: providing a light source L, providing the light source L comprising providing a blue light emitting diode, as indicated by block 1701; providing a detector assembly 140 for detecting the at least one characteristic of the marine environment 15, providing the detector assembly 140 comprising configuring a single photodiode 141 to detect stimulated bioluminescence and transmissivity in response to the light source L and configuring the detector assembly 140 to generate at least one detector assembly output signal responsive to at least one detected characteristic, as indicated by block 1702; and providing a transmitter, providing the transmitter comprising coupling the transmitter with the detector assembly for transmitting the at least one detector assembly output signal, as indicated by block 1703; detecting the at least one characteristic of a marine biosphere, thereby generating the at least one detector assembly output signal, as indicated by block 1704; and transmitting the at least one detector assembly output signal, as indicated by block 1705.

Still referring to FIG. 17, the step of detecting the at least one characteristic of a marine biosphere, as indicated by block 1704, comprises measuring both stimulated bioluminescence and fluid clarity (transmission) in response to the light source L by way of the single photodiode 141, such as a Hamamatsu, 5-mm$^2$ photodiode, e.g., to measure both the stimulated bioluminescence and the fluid clarity. Marine fluid is pulled into a light-tight chamber at a flow rate of approximately 250 mL/s. The photodiode 141 measures stimulated bioluminescence during the approximately 1.5 residence time in front of the photodiode. When the pump turns off eliminating turbulence, the photodiode 141 then measures fluid clarity within the chamber. Data is then dumped to a spreadsheet for viewing. A light source L comprises a blue LED being transmitted through the chamber volume, containing marine fluid, to the photodiode 141. Degradation of, or a decrease in, fluid transparency from a previous air measurement is then measured and displayed as percent transmission.

Still referring to FIG. 17, by using the alternative autonomous biobuoy system S, for which the photodetector assembly 140 comprises a single photodiode 141, the method M2 is a sensor capable of making dual measurements, e.g., both stimulated bioluminescence and fluid clarity (transmission). Dual measurements are an improvement over related art methods, which involve measuring bioluminescence with a photomultiplier tube and using a separate sensor to measure fluid transparency (transmissometer). The photodetector assembly 140, comprising a single photodiode 141, is much smaller and more robust than related biobuoy sensors. The method M2 further comprises attaching an environmental container, accommodating the entire communication package, data logging module, and rechargeable lithium iron phosphate battery, and solar charger, to a surface float above fluid surface 17; positioning the sensor (approximately 14 inches in length and approximately 2 inches in diameter) below the surface float at a depth of approximately 2.5 feet below the fluid surface 17; attaching two small 5-W solar panels adjacent a communications box to supply energy to the rechargeable battery; activating the system approximately every 30 minutes for a period of approximately 5 seconds to collect data, to store the data onboard, and to await remote cell phone access to download the data to a remote site via a "hot spot" linked to a laptop computer. The method M2 further comprises deploying a plurality of alternative autonomous biobuoy systems S to gather data relating to multiple geographic regions, such as the United States, Asia, and the Persian Gulf, for strategic planning in relation to oceanographic conditions in various areas of responsibility (AOR).

Understood is that many additional changes in the details, materials, steps, and arrangement of parts, which have been herein described and illustrated to explain the nature of the embodiment, may be made by those skilled in the art within the principle and scope of the embodiment as expressed in the appended claims.

What is claimed:

1. An autonomous biobuoy system for detecting characteristics of a marine environment, the system comprising:
    a light source comprising a blue light emitting diode;
    a detector assembly for detecting the at least one characteristic of the marine environment, the detector assembly comprising a single photodiode configured to detect stimulated bioluminescence and transmissivity in response to the light source, the detector assembly configured to generate at least one detector assembly output signal responsive to at least one detected characteristic; and
    a transmitter coupled with the detector assembly for transmitting the at least one detector assembly output signal.

2. The system of claim 1, further comprising:
a housing; and
an adjustable ballast coupled with the housing for controlling movement thereof in relation to the marine environment.

3. The system of claim 1, further comprising a rechargeable power supply operatively coupled with the detector assembly for powering thereof, the rechargeable power supply capable of powering a bilge pump and powering the detector assembly.

4. The system of claim 3, wherein the rechargeable power supply comprises at least one lithium phosphate iron battery.

5. The system of claim 3, further comprising at least one solar panel and at least one solar charger corresponding the rechargeable power supply, the at least one solar charger operatively coupled with rechargeable power supply for facilitating recharging thereof.

6. The system of claim 5, wherein the at least one solar panel comprises a plurality of solar panels.

7. The system of claim 5, further comprising an enclosure for accommodating and protecting at least one of the transmitter, the rechargeable power supply, a phone modem, a data logger, and the solar charger.

8. The system of claim 1, wherein the blue light emitting diode configured for masking by a filter for attenuation thereof, whereby saturation of the single photodiode is preventable.

9. The system of claim 1,
wherein the transmitter is configured communicate by at least one technology of 3G, 4G, 5G, and LTE, and
wherein data is downloadable from a remote location having hot spot access in relation to the Internet.

10. The system of claim 1, further comprising an adjustable ballast configured to adjust the depth of the housing for at least one deployment condition of a floating condition and a submersible condition.

11. A method of fabricating an autonomous biobuoy system for detecting characteristics of a marine environment, the method comprising:
Providing a light source, providing the light source comprising providing a blue emitting diode;
Providing a detector assembly for detecting the at least one characteristic of the marine environment, providing the detector assembly comprising configuring a single photodiode to detect stimulated bioluminescence and transmissivity in response to the light source and configuring the detector assembly to generate at least one detector assembly output signal response to at least one detected characteristic; and
Providing a transmitter, providing the transmitter comprising coupling the transmitter with the detector assembly for transmitting the at least one detector assembly output signal.

12. The method of claim 11, further comprising:
providing a housing; and
providing an adjustable ballast coupled with the housing for controlling movement thereof in relation to the marine environment.

13. The method of claim 11, further comprising providing a rechargeable power supply operatively coupled with the detector assembly for powering thereof, providing the rechargeable power supply comprising providing the rechargeable power supply as capable of powering a bilge pump and powering the detector assembly.

14. The method of claim 13, wherein providing the rechargeable power supply comprises providing at least one lithium phosphate iron battery.

15. The method of claim 13, further comprising providing at least one solar panel and providing at least one solar charger corresponding the rechargeable power supply, providing the at least one solar charger comprising operatively coupling the at least one solar charger with rechargeable power supply for facilitating recharging thereof.

16. The method of claim 15, wherein providing the at least one solar panel comprises providing a plurality of solar panels.

17. The method of claim 11, wherein providing the blue light emitting diode comprises masking the blue light emitting diode by a filter for attenuation thereof, whereby saturation of the photodiode is preventable.

18. The method of claim 15, further comprising:
providing an enclosure for accommodating and protecting at least one of the transmitter, the rechargeable power supply, a phone modem, a data logger, and the solar charger; and
providing an adjustable ballast configured to adjust the depth of the housing for at least one deployment condition of a floating condition and a submersible condition.

19. The method of claim 11,
wherein providing the transmitter comprises configuring the transmitter to communicate by at least one technology of 3G, 4G, 5G, and LTE, and
wherein providing the transmitter comprises configuring the transmitter to facilitate downloading data from a remote location having hot spot access in relation to the Internet.

20. A method for detecting at least one characteristic of a marine environment and transmitting at least one detector assembly output signal by way of an autonomous biobuoy system, the method comprising:
Providing an autonomous biobuoy system, providing the autonomous biobuoy system comprising:
Providing a light source, providing the light source comprising providing a blue light emitting diode,
Providing a detector assembly for detecting the at least one characteristic of the marine environment, providing the detector assembly comprising configuring a single photodiode to detect stimulated bioluminescence and transmissivity in response to the light source and configuring the detector assembly to generate at least one detector assembly output signal response to at least one detected characteristic; and
Providing a transmitter, providing the transmitter comprising coupling the transmitter with the detector assembly for transmitting the at least one detector assembly output signal;
Detecting the at least one characteristic of a marine environment, thereby generating the at least one detector assembly output signal; and
Transmitting the last least one detector assembly output signal.

* * * * *